(12) United States Patent
Pathak et al.

(10) Patent No.: US 11,786,309 B2
(45) Date of Patent: Oct. 17, 2023

(54) SYSTEM AND METHOD FOR FACILITATING DBS ELECTRODE TRAJECTORY PLANNING

(71) Applicant: ADVANCED NEUROMODULATION SYSTEMS, INC., Plano, TX (US)

(72) Inventors: Yagna Pathak, Skokie, IL (US); Simeng Zhang, Frisco, TX (US); Dehan Zhu, Plano, TX (US); Anahita Kyani, Plano, TX (US); Hyun-Joo Park, Frisco, TX (US); Erika Ross, Dallas, TX (US)

(73) Assignee: ADVANCED NEUROMODULATION SYSTEMS, INC., Plano, TX (US)

( * ) Notice: Subject to any disclaimer, the term of this patent is extended or adjusted under 35 U.S.C. 154(b) by 320 days.

(21) Appl. No.: 17/135,022

(22) Filed: Dec. 28, 2020

(65) Prior Publication Data

US 2022/0202491 A1 Jun. 30, 2022

(51) Int. Cl.
*A61B 34/10* (2016.01)
*G06T 7/70* (2017.01)
(Continued)

(52) U.S. Cl.
CPC .............. *A61B 34/10* (2016.02); *A61B 5/055* (2013.01); *A61B 6/032* (2013.01); *A61B 6/469* (2013.01);
(Continued)

(58) Field of Classification Search
CPC ......... A61B 34/10; A61B 6/032; A61B 6/469; A61B 6/501; A61B 6/5223; A61B 6/5247;
(Continued)

(56) References Cited

U.S. PATENT DOCUMENTS

| 2018/0110973 A1* | 4/2018 | Johnson | A61B 5/4836 |
| 2019/0090749 A1* | 3/2019 | Leuthardt | A61B 34/10 |

(Continued)

OTHER PUBLICATIONS

Pan D, Zeng A, Jia L, Huang Y, Frizzell T, Song X. Early Detection of Alzheimer's Disease Using Magnetic Resonance Imaging: A Novel Approach Combining Convolutional Neural Networks and Ensemble Learning. Front Neurosci. May 13, 2020;14:259. doi: 10.3389/fnins.2020.00259. (Year: 2020).*

(Continued)

*Primary Examiner* — Amandeep Saini
*Assistant Examiner* — Julius Chai
(74) *Attorney, Agent, or Firm* — Armstrong Teasdale LLP

(57) ABSTRACT

A system and method for facilitating DBS electrode trajectory planning using a machine learning (ML)-based feature identification scheme configured to identify and distinguish between various regions of interest (ROIs) and regions of avoidance (ROAs) in a patient's brain scan image. In one arrangement, standard orientation image slices as well as re-sliced images in non-standard orientations are provided in a labeled input dataset for training a CNN/ANN for distinguishing between ROIs and ROAs. Upon identification of the ROIs and ROAs in the patient's brain scan image, an optimal trajectory for implanting a DBS lead may be determined relative to a particular ROI while avoiding any ROAs.

14 Claims, 15 Drawing Sheets

(51) Int. Cl.
*G16H 30/40* (2018.01)
*G06V 10/25* (2022.01)
*A61B 5/055* (2006.01)
*A61B 6/03* (2006.01)
*A61B 6/00* (2006.01)
*G06N 3/08* (2023.01)
*G06T 7/00* (2017.01)
*G06F 18/214* (2023.01)
*A61N 1/05* (2006.01)

(52) U.S. Cl.
CPC ............ *A61B 6/501* (2013.01); *A61B 6/5223* (2013.01); *A61B 6/5247* (2013.01); *G06F 18/214* (2023.01); *G06N 3/08* (2013.01); *G06T 7/0014* (2013.01); *G06T 7/70* (2017.01); *G06V 10/25* (2022.01); *G16H 30/40* (2018.01); *A61B 2034/107* (2016.02); *A61B 2505/05* (2013.01); *A61N 1/0534* (2013.01); *G06T 2207/10081* (2013.01); *G06T 2207/10088* (2013.01); *G06T 2207/20081* (2013.01); *G06T 2207/20084* (2013.01); *G06T 2207/30016* (2013.01); *G06T 2207/30241* (2013.01); *G06V 2201/031* (2022.01)

(58) Field of Classification Search
CPC . A61B 2034/107; A61B 2505/05; G06T 7/70; G06T 7/0014; G06T 2207/10081; G06T 2207/10088; G06T 2207/20081; G06T 2207/20084; G06T 2207/30016; G06T 2207/30241; G16H 30/40; G06V 10/25; G06V 201/031; G06F 18/214; G06N 3/08; A61N 1/0534
See application file for complete search history.

(56) References Cited

U.S. PATENT DOCUMENTS

| | | | | |
|---|---|---|---|---|
| 2019/0142519 | A1* | 5/2019 | Siemionow | A61B 34/30 600/408 |
| 2020/0158805 | A1* | 5/2020 | Griswold | G01R 33/4806 |
| 2020/0297228 | A1* | 9/2020 | Crawford | A61B 5/6868 |
| 2021/0158515 | A1* | 5/2021 | Sullivan | G06T 7/11 |

OTHER PUBLICATIONS

Nalepa J, Marcinkiewicz M, Kawulok M. Data Augmentation for Brain-Tumor Segmentation: A Review. Front Comput Neurosci. Dec. 11, 2019;13:83. doi: 10.3389/fncom.2019.00083. PMID: 31920608; PMCID: PMC6917660. (Year: 2019).*
Park Seong-Cheol et al: "Deep Learning-Based Deep Brain Stimulation Targeting and Clinical Applications", Frontiers in Neuroscience, Book, Oct. 24, 2019, vol. 13.
Yiming Xiao et al; "Image guidance in deep brain stimulation surgery to treat Parkinson's disease: a review"; Website/Book, Mar. 10, 2020, Cornell University, Ithaca, NY 14853.
Pan Dan et al; "Early Detection of Alzheimer's Disease Using Magnetic Resonances Imaging: A Novel Approach Combining Convolution! Nerual Networks and Ensemble Learning" Frontiers in Neuroscience, Book, May 13, 2020, vol. 14.
Nalepa Jakub et al; "Data Augmentation for Brain-Tumor Segmentation: A Review",Frontiers in Computational Neuroscience, Website Article, Dec. 11, 2019, pp. 1-18 vol. 13.
Lundervold Alexander Selvikag et al; "An overview of deep learning in medical imagining focusing on MRI", Website Article, May 1, 2019, pp. 102-127, vol. 29, No. 2.
Anonymous, "Dilution (neural networks)—Wikipedia", Website, Dec. 12, 2020.
International Search Report and Written Opinion, PCT/US2021/064598, dated Apr. 12, 2022, 20 pages.

* cited by examiner

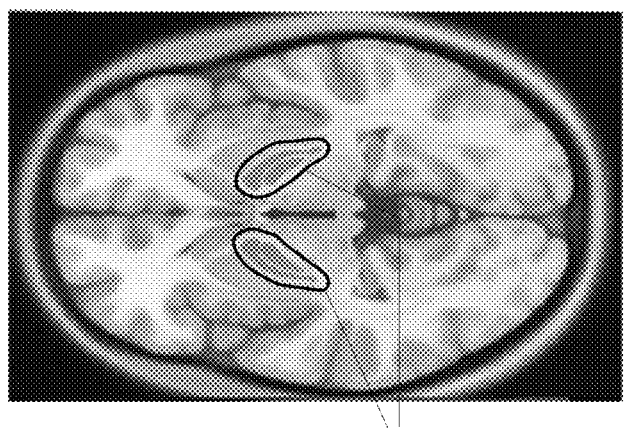
FIG. 1C-3 AXIAL
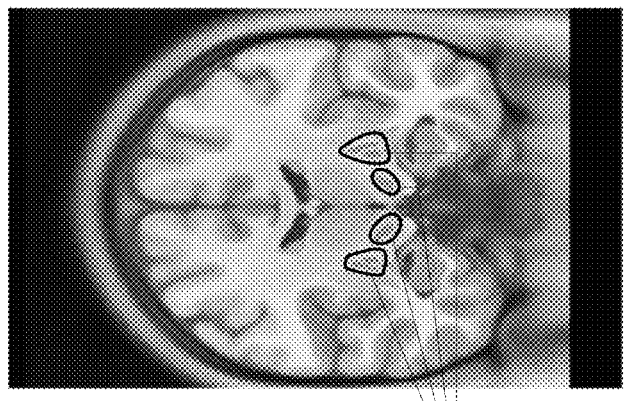
FIG. 1C-2 CORONAL
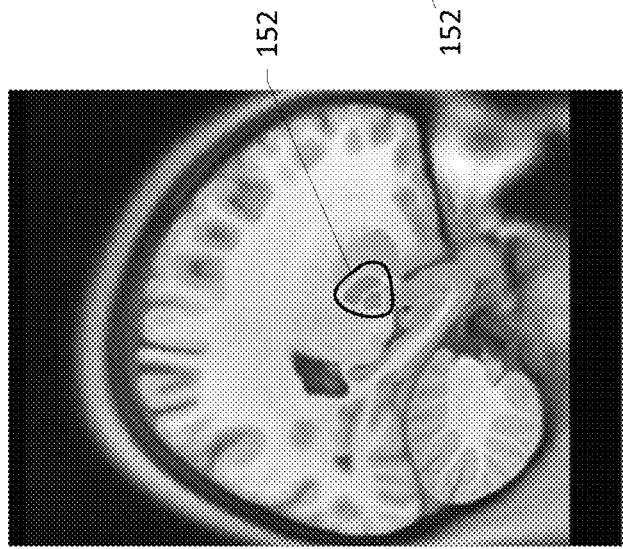
FIG. 1C-1 SAGITTAL

```
┌─────────────────────────────────────────────────────────────────────┐
│  OBTAINING A SET OF MEDICAL IMAGING DATA PERTAINING TO HUMAN CRANIAL │
│  ANATOMY, THE SET OF MEDICAL IMAGING DATA SAMPLED FROM A PLURALITY OF│
│  HUMANS IN ONE OR MORE IMAGING MODALITIES, WHEREIN THE MEDICAL IMAGING│
│  DATA COMPRISES IMAGE SLICES TAKEN ALONG AT LEAST ONE OF CORONAL, SAGITTAL│
│           AND AXIAL PLANES RELATIVE TO THE HUMAN CRANIAL ANATOMY     │
└─────────────────────────────────────────────────────────────────────┘
                                    │
                                    ▼                                 ⎯ 202
┌─────────────────────────────────────────────────────────────────────┐
│   PRE-PROCESSING IMAGE DATA INCLUDING, E.G., RE-SLICING AT LEAST A PORTION OF│
│     THE MEDICAL IMAGING DATA THROUGH ONE OR MORE PLANES THAT ARE AT AN│
│    ANGULAR ORIENTATION WITH RESPECT TO AT LEAST ONE OF THE CORONAL, SAGITTAL│
│       AND AXIAL PLANES, THEREBY OBTAINING A RE-SLICED MEDICAL IMAGING DATA│
│                              PORTION                                │
└─────────────────────────────────────────────────────────────────────┘
                                    │
                                    ▼                                 ⎯ 204
┌─────────────────────────────────────────────────────────────────────┐
│    TRAINING A FIRST ARTIFICIAL NEURAL NETWORK (ANN) ENGINE USING A PORTION│
│     OF THE MEDICAL IMAGING DATA THAT HAS NOT BEEN RE-SLICED AND A PORTION│
│    COMPRISING THE RE-SLICED MEDICAL IMAGING DATA, THE IMAGING DATA LABELED│
│    WITH APPROPRIATE STRUCTURAL LABELS, TO OBTAIN A VALIDATED AND TESTED ANN│
│    ENGINE CONFIGURED TO DISTINGUISH BETWEEN ONE OR MORE REGIONS OF INTEREST│
│        (ROI) FROM ONE OR MORE REGIONS OF AVOIDANCE (ROA) IN A HUMAN BRAIN IMAGE│
└─────────────────────────────────────────────────────────────────────┘
                                    │
                                    ▼                                 ⎯ 206
┌─────────────────────────────────────────────────────────────────────┐
│   EXECUTING THE FIRST VALIDATED/TESTED ANN ENGINE, IN RESPONSE TO AN INPUT│
│   IMAGE OF A PATIENT'S BRAIN OBTAINED USING A PARTICULAR IMAGING MODALITY,│
│    TO IDENTIFY AT LEAST ONE PARTICULAR ROI IN THE PATIENT'S BRAIN TO FACILITATE│
│   PLANNING OF AN OPTIMAL TRAJECTORY FOR IMPLANTING A DBS LEAD WITH ONE OR│
│    MORE ELECTRODES IN THE AT LEAST ONE PARTICULAR ROI WHILE AVOIDING ANY│
│                  ROAS IDENTIFIED IN THE PATIENT'S BRAIN             │
└─────────────────────────────────────────────────────────────────────┘
                                                                      ⎯ 208
           200A ⎯⎯⎯↗

FIG. 2A
```

```
┌─────────────────────────────────────────────────────────────────┐
│ BLENDING TWO OR MORE CO-REGISTERED AND/OR CO-RESOLUTION IMAGE   │
│ SLICES, E.G., FROM EITHER A PORTION OF THE MEDICAL IMAGING DATA │
│ THAT HAS NOT BEEN RE-SLICED AND/OR FROM THE PORTION COMPRISING  │
│ THE RE-SLICED MEDICAL IMAGING DATA, TO GENERATE HYBRID IMAGE    │
│ SLICES                                                          │
└─────────────────────────────────────────────────────────────────┘
                                                              └ 212
                              ▼
┌─────────────────────────────────────────────────────────────────┐
│ USING THE HYBRID IMAGE SLICES IN TRAINING, VALIDATING AND       │
│ TESTING THE FIRST ANN ENGINE AND/OR A SECOND ANN ENGINE         │
└─────────────────────────────────────────────────────────────────┘
                                                              └ 214
                              ▼
┌─────────────────────────────────────────────────────────────────┐
│ EXECUTING THE FIRST AND SECOND ANN ENGINES SEPARATELY WITH      │
│ RESPECT TO AN INPUT IMAGE TO OBTAIN TWO SEPARATE SETS OF ROI    │
│ AND ROA PREDICTIONS/IDENTIFICATIONS                             │
└─────────────────────────────────────────────────────────────────┘
                                                              └ 216
                              ▼
┌─────────────────────────────────────────────────────────────────┐
│ COMBINING THE SEPARATE SETS OF OF ROI AND ROA                   │
│ PREDICTIONS/IDENTIFICATIONS TO OBTAIN HIGHER QUALITY            │
│ PREDICTIONS/IDENTIFICATIONS                                     │
└─────────────────────────────────────────────────────────────────┘
                                                              └ 218
   200B ⟶
                           FIG. 2B

┌─────────────────────────────────────────────────────────────────┐
│ PERFORMING, PRIOR TO TRAINING FIRST AND/OR SECOND ANN ENGINES,  │
│ MORPHOLOGICAL IMAGE PROCESSING OF IMAGE SLICES WITH RESPECT TO  │
│ SPECIFIC ROI/ROA FEATURES E.G., EDGE DETECTION, CONTRAST        │
│ BOOSTING, SHAPE/STRUCTURE DETECTION, ETC.                       │
└─────────────────────────────────────────────────────────────────┘
                                                              └ 222
                              ▼
┌─────────────────────────────────────────────────────────────────┐
│ USING THE PROCESSED IMAGE SLICES IN TRAINING, VALIDATING AND    │
│ TESTING THE FIRST AND/OR SECOND ANN ENGINES                     │
└─────────────────────────────────────────────────────────────────┘
                                                              └ 224
   200C ⟶
                           FIG. 2C
```

```
┌─────────────────────────────────────────────────────────────────┐
│ PERFORMING A DROPOUT TECHNIQUE WITH RESPECT TO THE FIRST AND/OR │
│ SECOND ANN ENGINES, WHEREIN A SELECT NUMBER OF NEURONS OR NODES │
│ ARE DROPPED FROM A PARTICULAR NN LAYER FOR EACH TRAINING        │
│ ITERATION OR EPOCH                                              │
└─────────────────────────────────────────────────────────────────┘
                                                              ╲— 226
200D ⇗

FIG. 2D

┌─────────────────────────────────────────────────────────────────┐
│ BUILDING AN ELECTRODE SCENE WITH RESPECT TO A PARTICULAR ROI OF │
│ A PATIENT'S BRAIN IMAGE FOR PLACING A DBS LEAD HAVING ONE OR    │
│ MORE ELECTRODES THEREAT                                         │
└─────────────────────────────────────────────────────────────────┘
                                                              ╲— 232
                                 ↓
┌─────────────────────────────────────────────────────────────────┐
│ DETERMINE, CALCULATE, OR OTHERWISE ESTIMATE AN OPTIMAL TRAJECTORY│
│ PATH TO PLACE A PARTICULAR ELECTRODE OF THE DBS LEAD VIA IMPLANT│
│ AT THE CENTER OF OR PROXIMATE TO THE PARTICULAR ROI             │
└─────────────────────────────────────────────────────────────────┘
                                                              ╲— 234
200E ⇗

FIG. 2E

┌─────────────────────────────────────────────────────────────────┐
│ CO-REGISTERING A CT IMAGE OF THE PATIENT'S BRAIN WITH THE       │
│ ROI/ROA MRI IMAGE OF THE PATIENT'S BRAIN (E.G., A PRE-OPERATIVE │
│ OR AN INTRA-OPERATIVE MRI IMAGE                                 │
└─────────────────────────────────────────────────────────────────┘
                                                              ╲— 242
                                 ↓
┌─────────────────────────────────────────────────────────────────┐
│ OBTAINING AN ENTRY POINT COORDINATE SET AND A TARGET POINT      │
│ COORDINATE SET WITH RESPECT TO THE PATIENT'S BRAIN FOR          │
│ PERFORMING AN IMPLANT PROCEDURE TO IMPLANT THE DBS LEAD USING   │
│ THE OPTIMAL TRAJECTORY, WHEREIN THE ENTRY POINT COORDINATE SET  │
│ IS OPERATIVE TO IDENTIFY A BURR HOLE LOCATION ON THE PATIENT'S  │
│ CRANIUM AND THE TARGET POINT COORDINATE SET IS OPERATIVE TO     │
│ IDENTIFY A LOCATION RELATIVE TO THE AT LEAST ONE PARTICULAR ROI │
│ IN THE PATIENT'S BRAIN                                          │
└─────────────────────────────────────────────────────────────────┘
                                                              ╲— 244
200F ⇗

FIG. 2F
```

| PROVIDING THE ENTRY POINT COORDINATE SET, THE TARGET POINT COORDINATE SET AND DATA RELATING TO THE OPTIMAL TRAJECTORY TO A STEREOTACTIC SURGERY SYSTEM INCLUDING A GUIDING APPARATUS CONTAINING THE DBS LEAD |
|---|

↘ 252

| AUTOMATICALLY GUIDING THE DBS LEAD TO THE AT LEAST ONE PARTICULAR ROI BASED ON THE ENTRY POINT COORDINATE SET, THE TARGET POINT COORDINATE SET AND THE DATA RELATING TO THE OPTIMAL TRAJECTORY DATA TO PLACE THE PARTICULAR ELECTRODE PROXIMATE TO THE AT LEAST ONE PARTICULAR ROI |
|---|

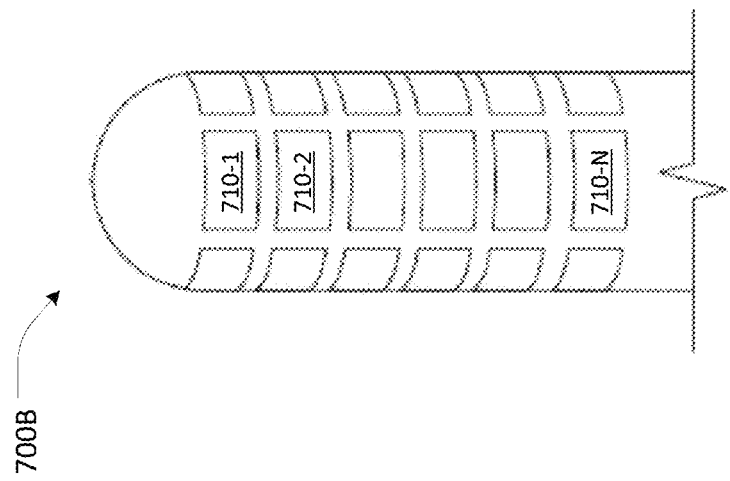
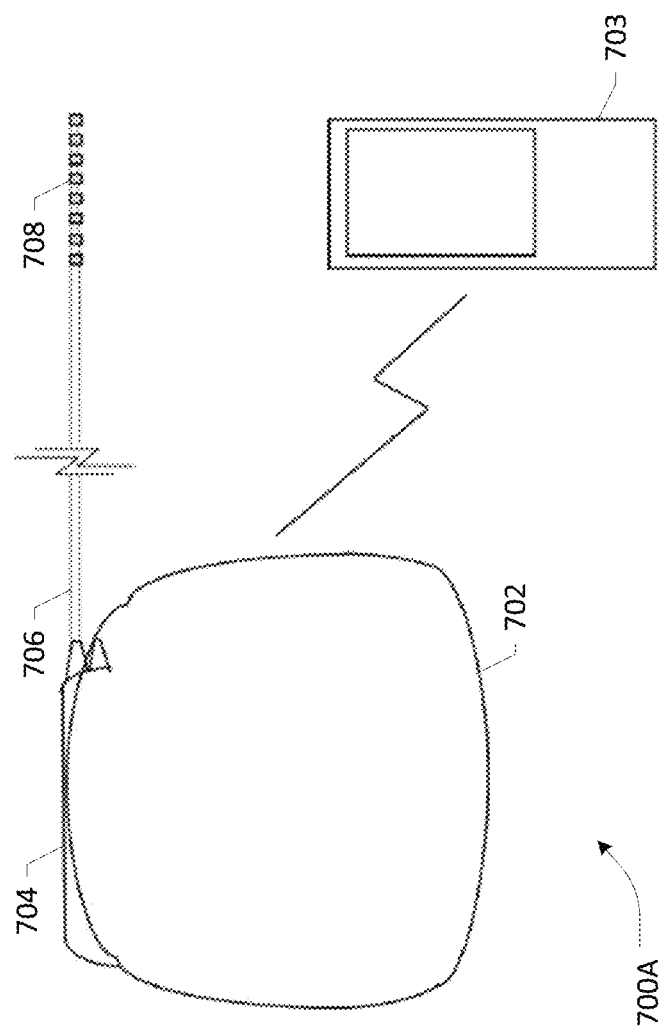
FIG. 7B
FIG. 7A

SYSTEM AND METHOD FOR FACILITATING DBS ELECTRODE TRAJECTORY PLANNING

TECHNICAL FIELD

The present disclosure generally relates to surgical procedures. More particularly, and not by way of any limitation, the present disclosure is directed to a system and method for facilitating electrode trajectory planning in deep brain stimulation (DBS) therapy applications.

BACKGROUND

Deep brain stimulation (DBS) refers to the delivery of electrical pulses into one or several specific sites within the brain of a patient to treat various neurological disorders. For example, deep brain stimulation has been proposed as a clinical technique for treatment of chronic pain, essential tremor, Parkinson's disease (PD), dystonia, epilepsy, depression, obsessive-compulsive disorder, and other disorders.

Brain anatomy typically requires precise targeting of tissue for stimulation by deep brain stimulation systems. For example, deep brain stimulation for Parkinson's disease commonly targets tissue within or close to the subthalamic nucleus (STN). The STN is a relatively small structure with diverse functions. Stimulation of undesired portions of the STN or immediately surrounding tissue can result in negative side effects. Mood and behavior dysregulation and other psychiatric effects have been reported from inaccurate stimulation of the STN in Parkinson's patients.

A deep brain stimulation procedure typically involves first obtaining preoperative images of the patient's brain (e.g., using computed tomography (CT) or magnetic resonance imaging (MRI)). Using the preoperative images, the neurosurgeon can select a target region within the brain, an entry point on the patient's skull, and a desired trajectory between the entry point and the target region. Because of the manual nature of identifying the target regions on a patient-by-patient basis, the existing procedures are usually time-consuming and expensive. Further, visual identification of potential target regions is often inaccurate, especially when the intended target is small and contains 3-dimensional (3D) functional subsystems that are hard to visualize on 2D images. Such challenges in combination with operation error can lead to incorrect implantation of a DBS electrode in the patient.

SUMMARY

Example embodiments of the present patent disclosure are directed to a system and method for facilitating DBS electrode trajectory planning using a machine learning (ML)-based feature identification scheme that advantageously identifies and distinguishes between various regions of interest (ROIs) and regions of avoidance (ROAs) in a patient's brain scan image on an individualized basis with minimal error in an efficient and robust manner while being readily generalizable and applicable to most patients.

In one aspect, an embodiment of a computer-implemented method of electrode trajectory planning for DBS therapy is disclosed. The claimed embodiment may comprise, inter alia, obtaining a set of medical imaging data pertaining to human cranial anatomy, the set of medical imaging data sampled from a plurality of humans in one or more imaging modalities, wherein the medical imaging data comprises image slices of the human brain taken along at least one of coronal, sagittal and transverse or axial planes relative to the human cranial anatomy. The claimed embodiment may further include effectuating one or more data augmentation and preprocessing techniques including, without limitation, re-slicing at least a portion of the medical imaging data through one or more planes that are at an angular orientation with respect to at least one of the coronal, sagittal and axial planes, thereby obtaining re-sliced medical imaging data. In one arrangement, one or more training datasets, validation datasets and/or testing datasets may be generated that may include at least a portion of the standard orientation image slices of the medical imaging data as well as the augmented/preprocessed medical imaging data, wherein the various structures of interest (e.g., ROAs, ROIs, etc), or collectively "targets," in general, may be appropriately labeled by human experts. According to some embodiments, a convolutional neural network (CNN) and/or an artificial neural network (ANN) based on deep learning techniques may be implemented as an ML-based image/feature identification scheme. In one arrangement, a first ANN engine may be trained using a portion of the labeled medical imaging data that has not been re-sliced and a portion of the re-sliced medical imaging data to obtain a validated and tested ANN engine configured to distinguish between one or more regions of interest (ROIs) from one or more regions of avoidance (ROA) in a human brain image. In one arrangement, the first ANN engine may be applied or executed in response to an input image of a patient's brain obtained using a particular imaging modality in order to identify at least one particular ROI in the patient's brain to facilitate planning of an optimal trajectory for implanting a DBS lead having one or more electrodes in the at least one particular ROI while avoiding any ROAs identified in the patient's brain.

In one variation, a data augmentation technique may involve blending two or more co-registered image slices selected from the standard orientation medical imaging data and/or re-sliced imaging data to obtain hybrid image slices. In one variation, one or more of the training, validation and test datasets may be populated with the hybrid image slices in order to enhance the predictive power of a trained ANN engine operative as an embodiment of the ML-based image/feature identification scheme.

In a further variation, after obtaining, identifying or otherwise predicting the structures of interest in the patient's brain image, an "electrode scene" may be built wherein a representation of a DBS electrode may be automatically generated relative to an optimal trajectory that targets the ROI. In one arrangement, path data relating to the optimal trajectory may be provided to a stereotactic surgery system that may use pre-operative CT image data for facilitating a DBS implant procedure.

In another aspect, an embodiment of a computer-implemented system of electrode trajectory planning for DBS therapy is disclosed, which comprises, inter alia, one or more processors, one or more input datasets including (pre)processed and augmented image data, and a persistent memory having program instructions stored thereon, wherein the program instructions, when executed by the one or more processors, are configured to perform one or more methods set forth herein.

In still further aspects, a non-transitory computer-readable medium or media containing computer-executable program instructions or code portions stored thereon is disclosed for performing example methods herein when executed by a processor entity of an apparatus.

Additional/alternative features and variations of the embodiments as well as the advantages thereof will be apparent in view of the following description and accompanying Figures.

BRIEF DESCRIPTION OF THE DRAWINGS

Embodiments of the present disclosure are illustrated by way of example, and not by way of limitation, in the Figures of the accompanying drawings in which like references indicate similar elements. It should be noted that different references to "an" or "one" embodiment in this disclosure are not necessarily to the same embodiment, and such references may mean at least one. Further, when a particular feature, structure, or characteristic is described in connection with an embodiment, it is submitted that it is within the knowledge of one skilled in the art to effectuate such feature, structure, or characteristic in connection with other embodiments whether or not explicitly described.

The accompanying drawings are incorporated into and form a part of the specification to illustrate one or more exemplary embodiments of the present disclosure. Various advantages and features of the disclosure will be understood from the following Detailed Description taken in connection with the appended claims and with reference to the attached drawing Figures in which:

FIGS. 1C-1 to 1C-3 depict example standard orientation sectional images in another imaging modality;

FIGS. 1D-1 to 1D-3 depict example re-sliced sectional images (e.g., along a non-standard orientation or plane) in one imaging modality;

FIGS. 2A-2G depict flowcharts illustrative of blocks, steps and/or acts that may be (re)combined in one or more arrangements with or without additional flowcharts of the present patent disclosure for facilitating a machine learning (ML)-based image identification scheme for identifying regions of interest (ROIs) and regions of avoidance (ROAs) in connection with electrode trajectory planning according to some embodiments of the present patent disclosure;

FIGS. 7A and 7B depict a DBS pulse generator and associated lead system having a plurality of electrodes that may be implanted using an image identification system according to an example embodiment of the present patent disclosure.

DETAILED DESCRIPTION

In the description herein for embodiments of the present disclosure, numerous specific details are provided, such as examples of circuits, devices, components and/or methods, to provide a thorough understanding of embodiments of the present disclosure. One skilled in the relevant art will recognize, however, that an embodiment of the disclosure can be practiced without one or more of the specific details, or with other apparatuses, systems, assemblies, methods, components, materials, parts, and/or the like set forth in reference to other embodiments herein. In other instances, well-known structures, materials, or operations are not specifically shown or described in detail to avoid obscuring aspects of embodiments of the present disclosure. Accordingly, it will be appreciated by one skilled in the art that the embodiments of the present disclosure may be practiced without such specific components. It should be further recognized that those of ordinary skill in the art, with the aid of the Detailed Description set forth herein and taking reference to the accompanying drawings, will be able to make and use one or more embodiments without undue experimentation.

Additionally, terms such as "coupled" and "connected," along with their derivatives, may be used in the following description, claims, or both. It should be understood that these terms are not necessarily intended as synonyms for each other. "Coupled" may be used to indicate that two or more elements, which may or may not be in direct physical or electrical contact with each other, co-operate or interact with each other. "Connected" may be used to indicate the establishment of communication, i.e., a communicative relationship, between two or more elements that are coupled with each other. Further, in one or more example embodiments set forth herein, generally speaking, an electrical element, component or module may be configured to perform a function if the element may be programmed for performing or otherwise structurally arranged to perform that function.

Figure 1A:
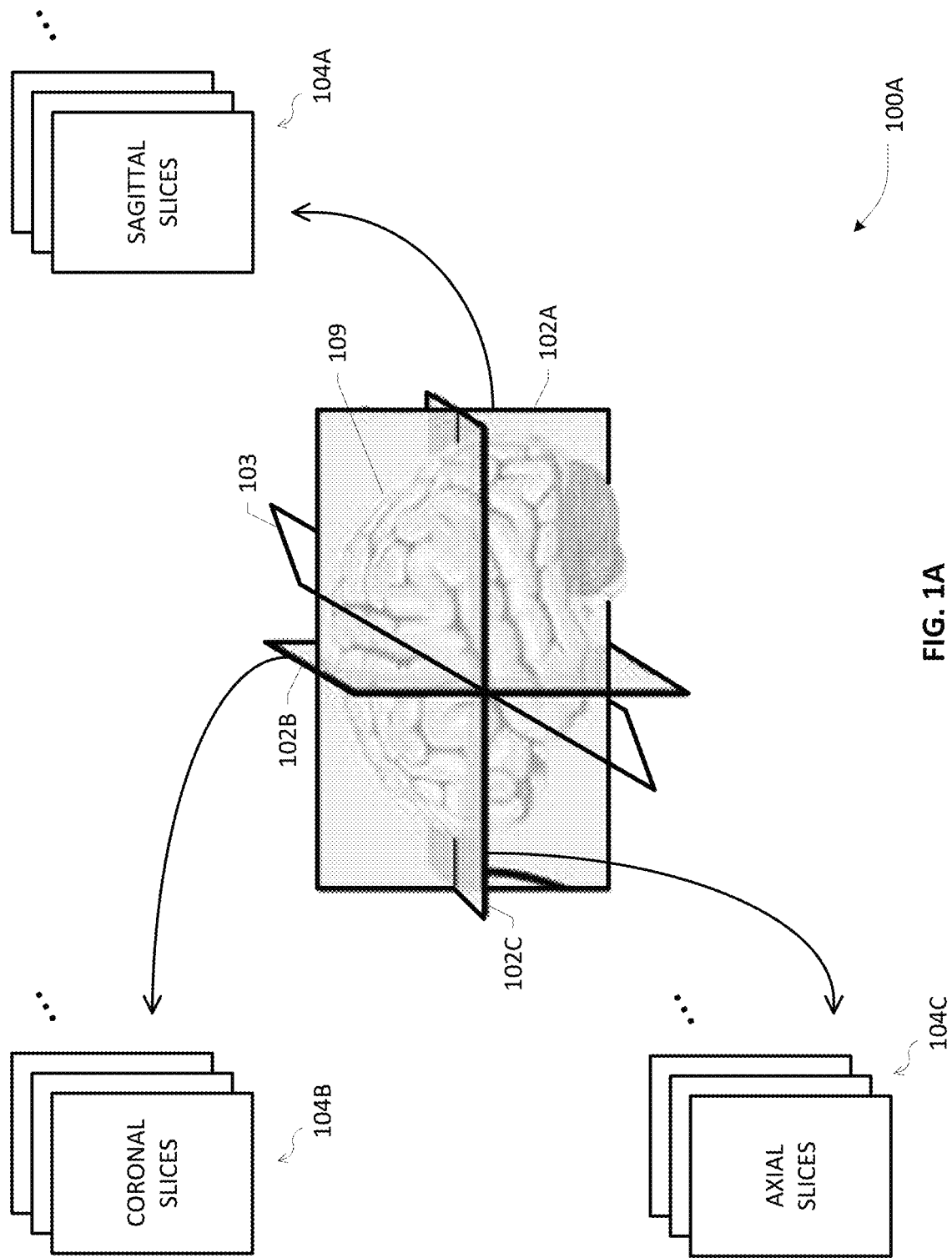
FIG. 1A depicts an example human brain anatomical coordination system for use in reference to standard orientation medical imaging data and/or processed medical imaging data wherein image slices may be obtained through multiple planes and orientations for purposes of some embodiments of the present patent disclosure.

FIG. 1A depicts an example human brain anatomical coordinate system for use in reference to medical imaging data that may be obtained through and/or along multiple planes and orientations with respect to human cranial anatomy in one or more imaging modalities, wherein image slices may be processed, preprocessed, or otherwise manipulated for purposes of some embodiments of the present patent disclosure. In general, imaging modalities may include but are not limited to: T1-weigthed magnetic resonance imaging (MRI) pre-contrast, T1-weigthed MRI post-contrast, T2-weighted MRI, MRI sequence with susceptibility-weighted imaging (SWI), diffusion tensor imaging (DTI) tractography, MR-angiography, MR-elastography, computed tomography (CT), etc. Although some example embodiments set forth below may be particularly described in reference to certain MRI-based modalities, it should be appreciated that the teachings herein are not necessarily limited thereto. In some arrangements, the medical imaging data of human brain anatomy may be obtained in one or more standard orientations relative to the three principal axes of a human body, e.g., latero-lateral (X), dorso-ventral (Y) and rostro-caudal (Z) axes, that give rise to three standard planes or sections with respect to human brain 109: a sagittal or medial section 102A, a coronal section 102B, and an axial or transverse section 102C as illustrated in image coordinate system 100A. A brain atlas database may be composed of images of several serial sections along different anatomical planes, wherein each relevant brain structure may be assigned a label and a number of coordinates to define its outline or volume. Images of serial sections taken along a standard anatomical plane are parallel to one another (e.g., having a uniform inter-slice separation), which may be referred to as standard slices, e.g., sagittal slices 104A, coronal slices 104B and axial slices 104C. In some arrangements, to facilitate comparative group analyses using functional imaging data, inter alia, the individual brain images may be transformed into a common coordinate space such as, e.g., the Talairach space, the Montreal Neurological Institute (MNI) space, etc., as known in the art.

Figures 1, 1B:
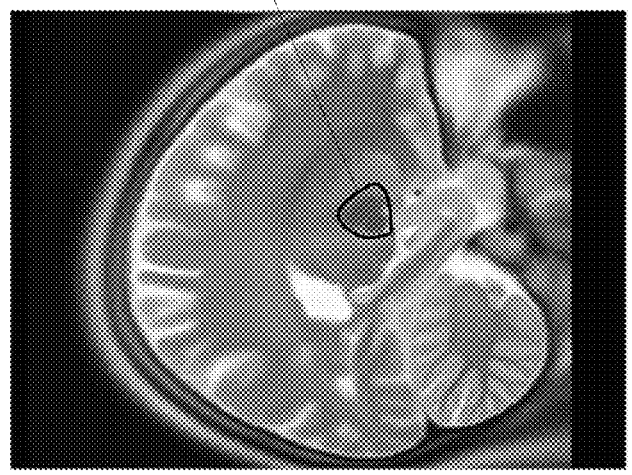
FIGS. 1B-1 to 1B-3 depict example standard orientation sectional images in one imaging modality.
Figures 1, 1B, 2:
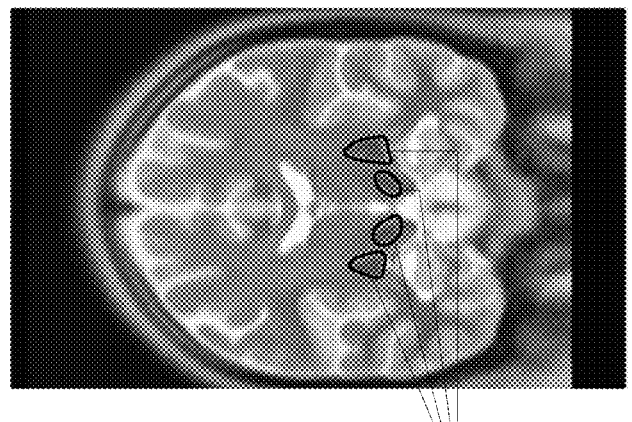
Figures 1, 1B, 2, 3:
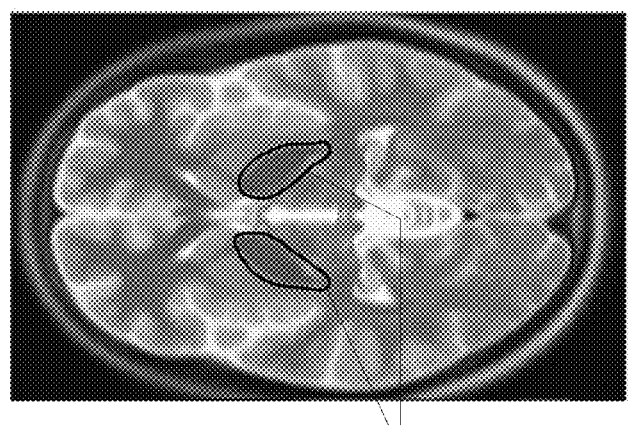
Figures 1, 1D, 2, 3:
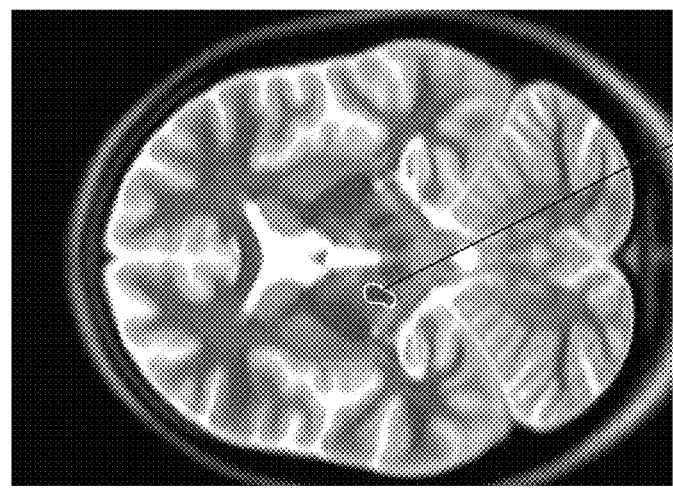
Figures 1, 1D, 2:
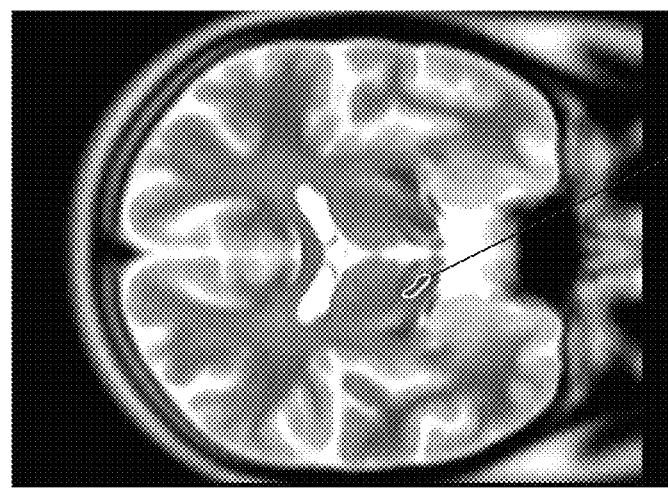
Figures 1, 1D:
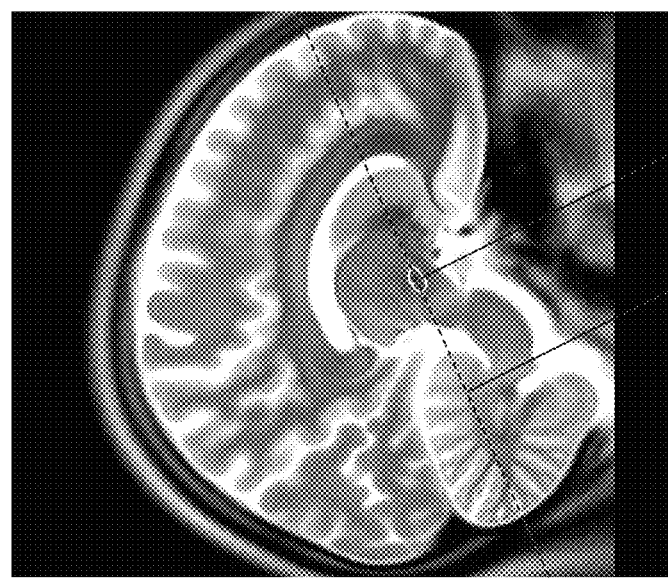

As will be seen further below, example embodiments may be configured to utilize a variety of data conditioning and/or image processing techniques and processes with respect to the standard medical imaging data, which may be used to generate one or more conditioned datasets for training, validating, and testing a suitable machine learning (ML)-based image identification/prediction process or engine for facilitating a reliable and effective DBS electrode trajectory planning scheme that overcomes the deficiencies and shortcomings of existing technologies as set forth elsewhere in the present patent disclosure. An example (pre)processing technique for purposes of some embodiments may involve "re-slicing" of one or more standard slices, e.g., image slices 104A-C, wherein a standard slice may be rotated or "visualized" in one or more different perspectives relative to the standard anatomical planes and/or the principal axes, whereby additional features, aspects, properties, or other image qualities of a brain structure of interest may be revealed in a fashion so as to enhance the input dataset quality. By way of illustration, a non-standard slice 103 is exemplified in FIG. 1 as a re-slice generated from a standard coronal slice having an angular orientation with respect to the coronal plane 102B. As will be apparent from the description further below, by improving the input dataset quality via re-slicing and other techniques (which may be collectively referred to as data augmentation or data perturbation) for purposes of training, validation and testing, a more efficient ML engine may be generated according to some example embodiments of the present patent disclosure.

In one arrangement, an example embodiment may therefore be configured to include the following processes, components, or subsystems: conditioning/preprocessing of medical imaging data; training, validating and testing an ML engine based on deep learning techniques, e.g., one or more artificial neural networks (ANNs) or convolutional neural networks (CNNs), hereinafter cumulatively and generally referred to as ANN or CNN in an interchangeable manner, unless otherwise specifically noted, that is operative as an intelligent image feature prediction system to identify various targets of interest (TOIs, also referred to as regions of interest or ROIs, or volumes of interest or VOIs) and targets of avoidance (TOAs, also referred to as regions of avoidance or ROAs, or volumes of avoidance or VOAs) based on available imaging data; applying or executing the trained ML engine with respect to a subject patient's image data to predict or otherwise identify particular ROIs and/or ROAs therein; and planning a optimal trajectory using the ROI/ROA location data for an electrode implant procedure.

Optionally, where a CT system is incorporated, an example embodiment may be configured to provide appropriate coordinate information to a stereotactic surgery system to facilitate the implant procedure either automatically and/or under the guidance of a surgeon. Skilled artisans will recognize that example ROIs may include, but are not limited to, the subthalamic nucleus (STN), internal globus pallidus (GPi), external GP (GPe), thalamus, anterior cingulate cortex, etc., which may be dependent on the type of stimulation therapy contemplated. In similar fashion, example ROAs may include but are not limited to brain structures such as, e.g., blood vessels, ventricles, and white matter tracts, etc.

FIGS. 1B-1 to 1B-3 depict example standard orientation sectional images in one imaging modality using T2-MRI that illustrate representative ROI(s) in multiple perspectives. In particular, image 100B-1 shows an example volume 152 containing STN and other basal ganglia nuclei in a sagittal section, image 100B-2 shows example volume 152 in a coronal section, and image 100B-3 shows example volume 152 in an axial section. FIGS. 1C-1 to 1C-3 depict example standard orientation sectional images in another imaging modality using T1-MRI that illustrate example volume 152 in a sagittal section 100C-1, a coronal section 100C-2 and an axial section 100C-3, respectively. FIGS. 1D-1 to 1D-3 depict example re-sliced sectional images (e.g., along a non-standard orientation or plane) in one imaging modality, e.g., T2-MRI. In particular, re-slicing may be performed along a primary axis plane in reference to a 3D coordinate system defined based on the location of a particular portion of example volume 152, e.g., STN 166, in addition to the planes orthogonal thereto. By way of example, a primary axis 162 is illustrated in image 100D-1 of FIG. 1D-1. Images 100D-2 and 100D-3 are sectional images relative to image 100D-1, shown respectively in FIGS. 100D-2 and 100D-3, each depicting STN 166 in a non-standard perspective. It will be apparent that various ROAs may also be identified and/or labeled in a similar manner in the foregoing sectional images regardless of the orientations.

FIGS. 2A-2G depict flowcharts illustrative of blocks, steps and/or acts that may be (re)combined in one or more arrangements with or without additional flowcharts of the present patent disclosure for facilitating ML-based image identification for identifying ROIs and ROAs in connection with electrode trajectory planning according to some embodiments of the present patent disclosure. Example process 200A of FIG. 2A may commence with obtaining a set of medical imaging data pertaining to human cranial/brain anatomy, wherein the medical imaging data comprises image slices taken along at least one of coronal, sagittal and transversal planes relative to the human brain anatomy (block 202). In one arrangement, the medical imaging data may be obtained from a plurality of humans in one or more imaging modalities that may be publicly available (e.g., as a brain atlas database). In another arrangement, the medical imaging data may comprise proprietary information. At block 204, a variety of data augmentation/pre-processing techniques, e.g., including re-slicing of the medical imaging data, may be performed. As previously noted, re-slicing may be performed with respect to each of the standard slices or at least a portion thereof of the medical imaging data, wherein re-sliced images through one or more planes that are at an angular orientation with respect to at least one of the coronal, sagittal and axial planes may be generated, thereby obtaining a re-sliced medical imaging data portion. Because a standard image slice may be angularly and/or pivotally rotated around a principal axis in a variety of orientations, theoretically an infinite number of re-sliced images may be obtained for each standard image slice. It will be appreciated, however, that additional useful information that may be obtained from generating extra re-slices may progressively diminish. Accordingly, due to practical utility considerations, only a relatively small number of re-sliced images may be generated with respect to a particular standard slice in an example embodiment. Further, the re-slicing does not have to be uniform throughout the human cranial anatomy, e.g., a re-sliced image may be at a higher resolution near the ROIs, and preferably in orientations that enhances the target view. In a further arrangement, a re-slicing orientation may be selected based on the ROIs, e.g., slices parallel to STN, GPi, etc. An example embodiment may therefore be advantageously configured such that appropriate re-slicing may be performed not only to ensure that various ROIs/ROAs are visible from multiple angles for facilitating the training of an ML-based image identification and prediction engine in a more efficient way but also to help enhance the predictive accuracy of the resultant ML engine.

In one arrangement, deep learning techniques (e.g., ANNs, CNNs, etc.) may be employed to facilitate automatic segmentation of ROIs and ROAs of human brain images, as previously noted. Depending on implementation, example neural networks may be configured to utilize parameterized, sparsely connected kernels which preserve the spatial characteristics of images. An example CNN may be trained, validated and tested on a suitably conditioned input dataset (e.g., a training dataset) in order to classify the pixels of input images into various ROIs such as the subthalamic nucleus, globus pallidus, thalamus, anterior cingulate cortex, etc., as noted above. It will be apparent to one skilled in the art upon reference hereto that the various ROIs and ROAs may be appropriately labeled in the input dataset images by human experts (e.g., neuroradiologists) and/or artificial intelligence (AI)-based expert systems, wherein the input dataset(s) may be partitioned into separate training, validation and testing datasets with correct labeling. Furthermore, such training datasets may include standard slices as well as re-sliced images obtained from different imaging modalities including but not limited to T1-weighted MRI pre-contrast, T1-weighted MRI post-contrast, T2-weighted MRI, SWI, DTI, tractography, MR-angiography, MR-elastography, CT, etc., as previously noted, including other imaging technologies such as isocentric fluoroscopy, bi-plane fluroscopy, MRI-associated 4D imaging (e.g., using movement or flow as the fourth dimension), optical coherence tomography (OCT), planar gamma scintigraphy (PGS), functional imaging techniques such as positron emission tomography (PET), single-photon emission computerized tomography (SPECTscan), functional MRI, magnetic source imaging (MSI) or magnetoencephalography (MEG), and the like. Some embodiments may involve still further types of image acquisition technologies such as 3D-transcranial ultrasound (TCU), contrast enhanced TCU, and so on. As will be seen further below, one or more CNNs/ANNs may be may be generated and trained on various types of training datasets, validation datasets and testing datasets, wherein appropriate data augmentation techniques may be applied depending on the imaging modalities.

In some embodiments, a first ANN engine may be trained using a portion of the medical imaging data that has not been re-sliced as well as a portion comprising the re-sliced medical imaging data to obtain a validated and tested ANN engine configured to distinguish between one or more ROIs from one or more ROAs in a human brain image, as set forth at block 206. At block 208, the first validated/tested ANN engine may be executed, for example, in response to an input image of a patient's brain obtained using a particular imaging modality, to identify at least one particular ROI in the patient's brain to facilitate planning of an optimal trajectory for implanting a DBS lead with one or more electrodes in the at least one particular ROI while avoiding any ROAs identified in the patient's brain.

In some example embodiments, one or more hybrid image blending techniques may be employed as part of data augmentation and conditioning with respect to the input image datasets used for training, validation and testing of a CNN engine. For example, two or more medical images may be blended into "hybrid" images and used as additional input data for training the CNN engine. Alternatively and/or additionally, an entirely new CNN engine may be trained to exclusively recognize such hybrid images. In such an arrangement, the predicted segmentation results (i.e., separated sets of ROIs and ROAs in an image) from the hybrid-imaging CNN engine may be combined with the segmentation results produced by the standard-imaging CNN engine to improve prediction results.

In some arrangements, the exact type of image blending may depend on the available data types, imaging modalities, particular ROI(s)/ROA(s), or a combination thereof. For example, a weighted sum of T1 and T2 MRI slices may be used (e.g., as a linear weighting) to create a T1-T2 hybrid image. If the targets are ROAs, e.g., the white matter tracks, an example embodiment may be configured to weigh the T1 image more heavily. On the other hand, if the target is a nucleus such as the STN (which is an ROI), the T2 image may be accorded a heavier weight in one example embodiment. If SWI images are available, they can also be added to the linear sum (and provided a heavier weight) in one arrangement to recognize nuclei such as STN. In addition to weighted linear summation, a ratio of two modalities (such as T1 and T2) can also be used to highlight specific features such as ventricles or myelination.

Accordingly, it should be appreciated that hybrid images can be a combination of any modalities depending on implementation, e.g., MRI+CT; MRI+CT+DTI; MRI+X-ray, etc. Further, the resolution of images may be up-sampled or down-sampled to combine in some arrangements. In still further arrangements, an example embodiment may be configured to combine and blend images that are co-registered and in the same resolution after (pre)processing. Although it is theoretically possible to combine images that are not in the same orientation or not co-registered (i.e., linear translation), such blending may not yield hybrid images that are sufficiently informative, and therefore may not be implemented in some arrangements. Moreover, both standard orientation images as well as re-sliced images may be blended to generate hybrid images in different combinations that may be used as part of any of the training, validation and/or testing datasets according to some embodiments of the present patent disclosure.

Example process 200B shown in FIG. 2B is illustrative of some of the foregoing variations that may be practiced optionally according to some embodiments. At block 212, two or more co-registered and/or co-resolution image slices may be blended, e.g., selected from either a portion of the medical imaging data that has not been re-sliced and/or from the portion comprising the re-sliced medical imaging data, in order to generate one or more hybrid image slices. At block 214, at least a portion of the hybrid image slices may be used in training, validating and testing the first ANN engine and/or a second ANN engine. Where a separate second ANN engine is utilized, the first and second ANN engines may be executed separately with respect to an input image of a patient's brain to obtain two separate sets of ROI and ROA predictions/identifications (block 216). Thereafter, the separate sets of ROIs and ROA predictions/identifications may be combined to obtain higher quality predictions/identifications, as set forth at block 218.

In some arrangements, input image datasets may be comprised of binary images that may contain certain imperfections that need to be rectified prior to using in ML training. In particular, the binary regions produced in an image by simple thresholding may be distorted by noise and texture. Some embodiments of the present patent disclosure may therefore employ various morphological image processing techniques as part of data augmentation and conditioning. As set forth at block 222, an example process 200C shown in FIG. 2C may involve, prior to training either a first and/or second ANN engines (e.g., where a separate ANN engine is provided with respect to blended images as set forth above), morphological image processing of image slices with respect to specific ROI/ROA features e.g., edge detection, contrast boosting, shape/structure detection, etc. At block 224, example process 200C may use the processed image slices in training, validating and testing the first and/or second ANN engines. An example embodiment may therefore be configured to employ morphological image processing as a collection of nonlinear operations related to the shape or morphology of features in an image. In some embodiments, such morphological operations may primarily rely on the relative ordering of pixel values, not on their numerical values, and may therefore be especially suited to the processing of binary images. Morphological operations can be applied to grayscale images as well as colorized images (e.g., false coloring), depending on the imaging modality. In one arrangement, an example morphological operations may comprise erosion, dilation, opening and closing with respect to sets of pixels using such concepts as size, shape, convexity, connectivity, and geodesic distance, etc.

According to some embodiments, therefore, any combination of the foregoing techniques may be used on any of the images or blended images, regardless of whether the images comprise re-sliced images or are of standard orientation, in order to highlight the ROIs/ROAs. Such processed images may be re-sliced and input as part of the training/testing of the ANN engine, or developed into a separate ANN engine to enhance prediction, similar to the use of a second ANN engine with respect the blended images as described above.

In still further arrangements, certain additional and/or alternative data augmentation and/or generalization techniques may be selectively or optionally applied on the training datasets. For example, techniques such as directional slicing may be used as a data perturbation process to enhance the input data pool for the neural network modeling and training. It should be appreciated that feeding input data images in all orientations (2D, 3D, or both) can help ensure that the ANN engine has a better representation of the targets. Further, in order to prepare the network for noisy data and possible overlap of targets, a dropout technique may be applied in an example embodiment. As exemplified at block 226 of example process 200D illustrated in FIG. 2D, a dropout technique may be performed with respect to any of the ANN engines, (e.g., the first and/or second ANN engines described above), wherein a select number of neurons or nodes are dropped from a particular neural network layer for each training iteration or epoch. In particular, such a scheme is operative to remove from weights calculation a random number of connections, which may change for each training pass (i.e., epoch) of an ANN engine, as will be set forth further below.

Additionally, if multiple datasets are available for the same subject, multiple representations of the same structure can be presented and labeled on the different sets of data. For example, blood vessels can be identified on T1-weighted post-contrast MRI as well as T2-weighted MRI of the same subject. In one embodiment, all the classes/labels may be used to train the neural network. In still further embodiments, techniques such as transfer learning (a machine learning process where a model developed for a task is reused as the starting point for a model on a second task) may be employed to utilize a pre-trained neural network on other brain data (such as detection of brain tumor), unfreeze the last few layers of the hidden layers, and train on a dataset to be used for DBS electrode trajectory planning. Skilled artisans will recognize that employing such transfer learning techniques may help a neural network for DBS electrode trajectory planning converge faster and perform ROA/ROI predictions with higher accuracy.

Example processes 200E-200G shown in FIGS. 2E-2G, respectively, are illustrative of additional and/or alternative aspects that may be selectively or optionally implemented in some embodiments of the present patent disclosure. In some arrangements, for example, a virtual "electrode scene" may be built with respect to a patient's brain image after obtaining the prediction(s) of ROIs/ROAs therein for placing a DBS lead therein, as set forth at block 232 of process 200E, wherein an example DBS lead may comprise one or more electrodes that may be segmented or otherwise, as will be set forth in further detail below. In one implementation, a representation of a selected electrode (e.g., a graphic symbol, pictorial image, pictogram, or an icon, etc. associated therewith) may be automatically generated at a path that hits or terminates at a specific location of a selected ROI (e.g., the center of the target region) while avoiding the ROAs such as, e.g., blood vessels, ventricles, etc. Given the respective locations of the ROIs and ROAs identified in reference to a known coordinate system, any known or heretofore unknown path optimization process may be executed to calculate, obtain, estimate or otherwise determine an optimal trajectory, as set forth at block 234. Additionally, alternatively or optionally, the user (e.g., a clinician or a medical technician) may specify the location of a certain electrode, or a segment (or segments) thereof, in relation to a particular target of interest by modifying the automatically generated electrode scene. Responsive thereto, the path optimization process may be configured to recalculate the path and update the trajectory accordingly.

In an arrangement where a CT imaging system is configured to interoperate with an example ML-based image identification system of the present patent disclosure as part of a stereotactic surgery system including a trajectory guiding apparatus, additional features and aspects may be implemented according to some embodiments herein. For example, if a pre-operational CT scan of a patient's brain is available, the CT scan may be co-registered to the patient's MRI scan as set forth at block 242 of process 200F shown in FIG. 2F. Depending on the stereotactic system used, an embodiment may be configured to output one or more coordinates for facilitating the stereotactic surgical procedure with respect to implanting a DBS lead. For example, an entry point coordinate set and a target point coordinate set with respect to the patient's brain may be obtained and/or generated for performing an implant procedure to implant the DBS lead using the optimal trajectory. As one skilled in the art will recognize, the entry point coordinate set may be operative to identify a burr hole location on the patient's cranium and the target point coordinate set may be operative to identify a location relative to at least one particular ROI in the patient's brain, as set forth at block 244. Further, the trajectory data comprising the entry point coordinate set, target point coordinate set, as well as any data relating to the optimal trajectory that may be converted to data suitable for controlling and/or configuring a guiding apparatus may be provided in real time to the stereotactic surgical station, as set forth at block 252 of process 200G shown in FIG. 2G. Responsive thereto, the DBS lead may be automatically guided and advanced to the ROI based on the target coordinate data to place the particular electrode proximate to the ROI at the indicated location (block 254).

Although an example implementation of the foregoing arrangement may be configured to be fully automatic, human intervention (e.g., a clinician or a medical technician) can be applied at various steps of target segmentation and trajectory planning (e.g., to fine-tune a lead trajectory in situ). In some embodiments, the ML-building process of the present patent disclosure may be supervised such that any human interactions to alter or otherwise modify a calculated path may be provided as real time feedback whereby the learning aspect of the ANN engine may be triggered for iteratively improving the ANN performance based on user preference and in situ adjustment information.

Figure 3A:
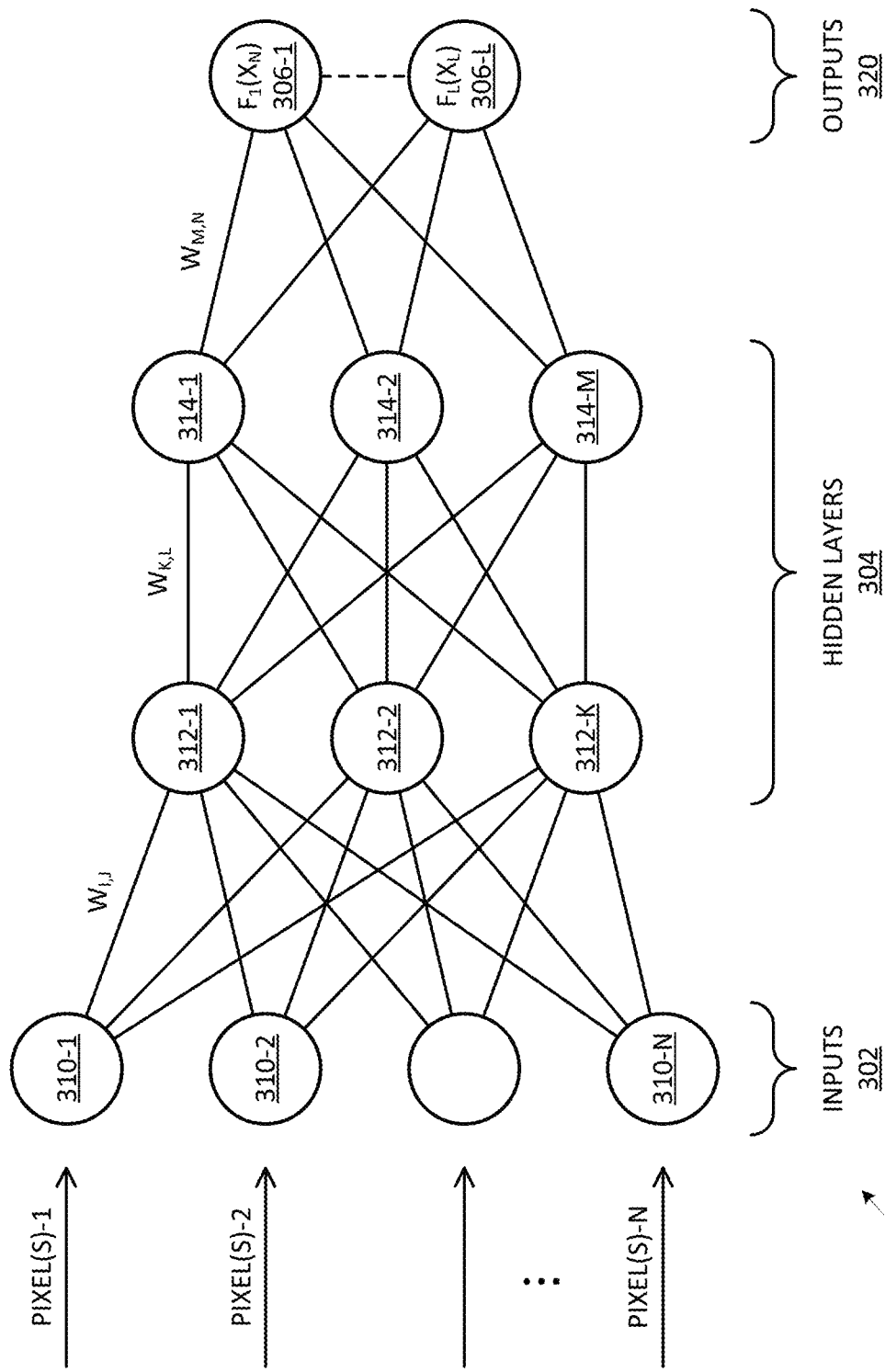
FIGS. 3A and 3B depict generalized artificial neural network (ANN) and convolution neural network (CNN) models operative as an ML-based process or engine for identifying or predicting ROIs and ROAs according to some embodiments of the present patent disclosure.
Figure 3B:
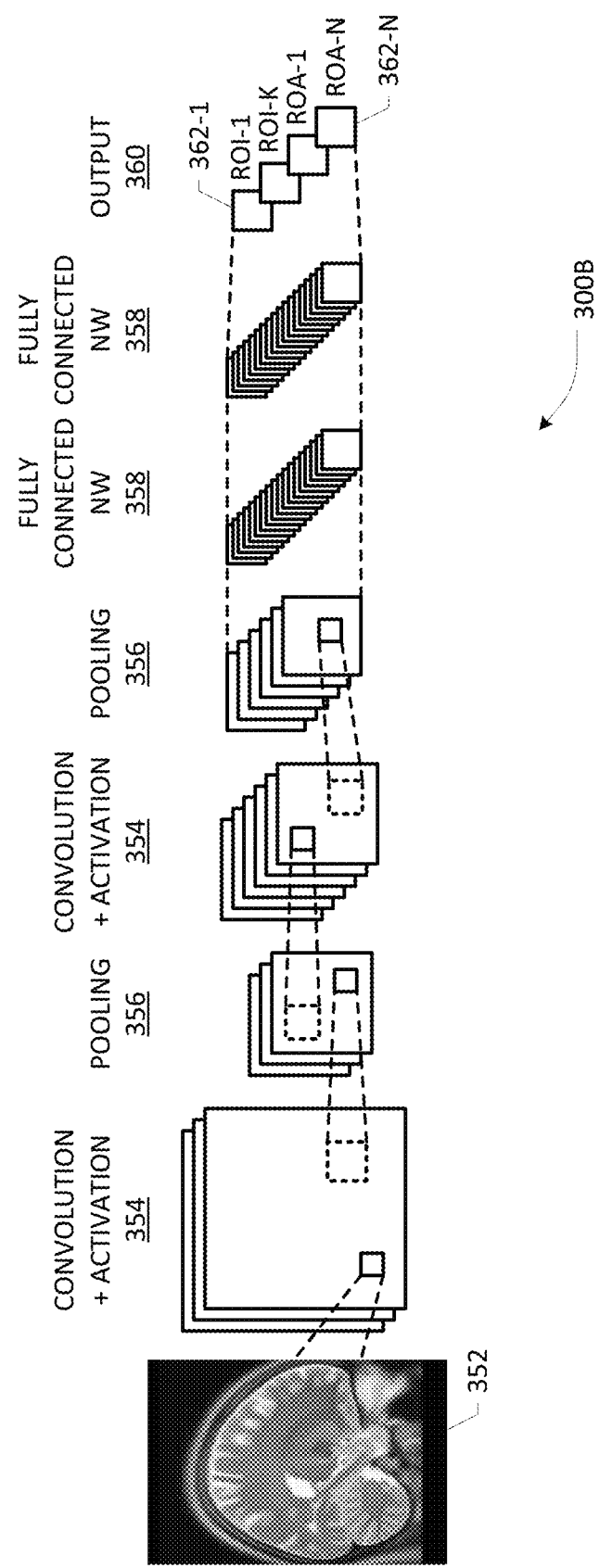

FIGS. 3A and 3B depict generalized ANN and CNN models operative as an ML-based process or engine for identifying or predicting ROIs and ROAs according to some embodiments of the present patent disclosure. As exemplified, ANN model 300A is operative in response to a plurality of pixels or pixel groups of an image having a plurality of labeled features, structures or regions that require identification. Input pixels may be provided to a corresponding input "neuron" or computational node 310-1 to 310-N that forms part of an input layer 302. Typically, ANN model 300A may be configured such that the nodes of the input layer 302 are passive, in that they do not modify the data. Rather, they receive a single value on their input, and duplicate the value to their respective multiple outputs, which may depend on the connectivity of the ANN model 300A. One or more hidden layers 304 may be provided for reducing the dimensionality of the input feature parametric space, wherein each of hidden nodes 312-1 to 312-K and 314-1 to 314-M are active, i.e., they modify the incoming data received from the prior layer nodes and output a value based on a functional computation involving weighted incoming data. In a fully interconnected ANN structure, each value from an input layer may be duplicated and sent to all of the hidden nodes. Regardless of the extent of the interconnectivity, the values entering a hidden node at any given hidden layer may be multiplied by weights, which comprise a set of predetermined numbers stored in the engine that may be "learned" in a series of iterative stages involving, e.g., output error back propagation or other methodologies. At each respective hidden node, the weighted inputs are added to produce a single intermediate value, which may be transformed through a suitable mathematical function (e.g. a nonlinear function, also referred to as an activation function) to generate an intermediate output between a normalized range (e.g., between 0 and 1). Depending on the number of hidden layers, weighted intermediate outputs may be provided to a next layer, and so on, until reaching an output layer 320 comprising one or more output nodes 306-1 to 306-L, which may be configured as a vector of values or probabilities identifying or predicting to which class or labeled structure a group of pixels belong.

Whereas neural networks can have any number of layers, and any number of nodes per layer, an example ANN model 300A may be configured with a fairly small number of layers, comprising only a portion of the size of the input layer. In the example arrangement shown in FIG. 3A, two hidden layers and an active output layer are shown, with inputs to first and second hidden layer nodes being modulated by weights $\{W_{i,j}\}$ and $\{W_{k,l}\}$ respectively, and inputs to the output node being modulated by weights $\{W_{m,n}\}$. The weights required to make example ANN model 300A to carry out a particular task, e.g., feature/image recognition, may be found by a learning algorithm, together with examples of how the system should operate in certain implementations.

As noted above, a fully-connected ANN engine involves every neuron in one layer connecting to all the neurons in the next layer. It is known, however, that a fully-connected network architecture is inefficient when it comes to processing image data because of various reasons. For example, for an average image with hundreds of pixels and two or three color channels, a traditional neural network may generate millions of parameters, which can lead to overfitting in addition to giving rise to computational inefficiency. Furthermore, it may be difficult to interpret results, debug and tune the model to improve its performance in an efficient manner. Accordingly, some embodiments may involve an overfitting-prevention technique such as a dropout technique in training a neural network, which randomly selects a subset of neurons and drops the rest neurons of a certain NN layer for each training epoch. This ensures that each epoch will be trained with a different set of neurons, and therefore regularizes the model and help prevent overfitting.

Unlike a fully connected neural network, a CNN engine (also sometimes referred to as a ConvNet) may be configured in which the neurons in one layer do not connect to all the neurons in the next layer. Rather, a CNN engine uses a three-dimensional structure, where each set of neurons analyzes a specific region or "feature" of the image. In one arrangement, a CNN model may filter connections by proximity (e.g., pixels may only be analyzed in relation to pixels nearby), making the training process computationally achievable. In a CNN process, therefore, each group of neurons may be configured to focus on one part of the image, e.g., a labeled structure or region. For example, there may be several stages of segmentation in which the process may be configured to smaller parts of the images until a final output comprising a vector of probabilities, which predicts, for each feature in the image, how likely it is to belong to a class or category.

Turning to FIG. 3B, depicted therein is an example CNN scheme 300B that may be operative as an ML-based image identification process for purposes of the present patent disclosure according to some embodiments. In operation, a CNN process takes advantage of the fact that the input consists of images and they constrain the architecture in a more sensible way. In particular, unlike a regular neural network, the layers of a CNN may have neurons arranged in three dimensions: width, height, and depth, where the term "depth" herein refers to the third dimension of an activation volume (e.g., depending on the number of color or grayscale channels), not to the depth of a full neural network, which can refer to the total number of layers in a network. Typically, the neurons in a layer will only be connected to a small region of the layer before it, instead of all of the neurons in a fully-connected manner, as previously noted.

Example CNN process 300B may be architected as a sequence of layers, wherein every layer is operative to transform one volume of activations through a differentiable function that may or may not have parameters. Three main types of layers may be provided in example CNN process 300B: convolutional layer with activation, pooling layer, and a fully-connected layer (e.g., similar to a regular neural network described above), wherein an input image 352 may be sequentially processed to yield a final output vector of class/label scores. By way of illustration, one or more convolution/activation layers 354 may be interspersed with one or more pooling layers 356, which may feed into one or more fully-connected (FC) layers 358 that generate output 360 of ROI/ROA prediction/identification scores 362-1 to 362-N. A convolution layer 354 may be configured to compute the output of neurons that are connected to local regions in the input or preceding layer, each computing a dot product between their weights and a small region they are connected to in the input volume. An activation layer associated with convolution layer 354 may be configured to apply an element-wise activation function such as a rectified linear unit or ReLu (e.g., max{0,x}). A pooling layer 356 may be operative to perform a down-sampling operation along the spatial dimensions (width and height). An FC layer 358 is operative as an ordinary ANN where each neuron therein is connected to all the members of the previous volume, with the final layer generating the ROI/ROA prediction output 360.

In the foregoing manner, example CNN process 300B is operative to transform the original image layer by layer from the original pixel values to the final class scores. It should be appreciated that whereas some layers of CNN process 300B may contain parameters, other layer may not. In particular, the convolution and FC layers perform transformations that are a function of not only the activations in the input volume, but also of the parameters (e.g., the weights and biases of the neurons). On the other hand, the activation and pooling layers may be configured to implement a fixed function. Generally, the parameters in the convolution and FC layers may will be trained with a gradient descent process so that the class scores that CNN process 300B computes are consistent with the labels in the training set for each image.

Regardless of whether ANNs and/or CNNs are used in an ML-based image recognition scheme of the present patent disclosure, certain image data preprocessing techniques and data augmentation processes may be implemented to improve the quality of input datasets as noted previously. Additional parameters and considerations for image data preparation may be set forth as below for purposes of some embodiments:

Image size: higher quality images give the model more information but require more neural network nodes and more computing power to process.

The number of images: the more data provided to a model, the more accurate it will be, while ensuring that the training set represents the real population.

The number of channels: grayscale images have two channels (black and white) and color images typically have three color channels (Red, Green, Blue or RGB), with colors represented in the range [0,255]. Depending on the image modalities, an example ML-based image recognition system may use input data images that may be comprised of grayscale images and/or color channels in some embodiments. Further, depending on the image modality and number of channels, different re-slicing, hybrid image blending and/or morphological image processing techniques or combinations thereof may also be employed.

Aspect ratio: ensures that the images have the same aspect ratio and size. Whereas some embodiments may require input images having a square shape, it is not necessary for other embodiments of the present patent disclosure.

Image scaling: as noted previously, input images (comprising standard slices, re-sliced images, hybrid images, etc.) may be up-scaled or down-scaled using a variety of techniques that may be available as image processing functions in deep learning libraries.

Statistical distributions of input image data: for example, parameters such as mean, standard deviation of image data for input pixels may be obtained by calculating the mean values for each pixel, in one or more training examples, to obtain information on the underlying structure in the images.

Normalizing image inputs: ensures that all input parameters (pixels in example embodiments) have a uniform data distribution. Skilled artisans will recognize that such data normalization may help achieve faster rates of convergence when training the ML engine.

Dimensionality reduction: techniques may be applied to collapse the RGB channels into a grayscale channel in some embodiments. Still further embodiments may involve reduction in other dimensions in order to render training less computationally intensive.

Figure 4:
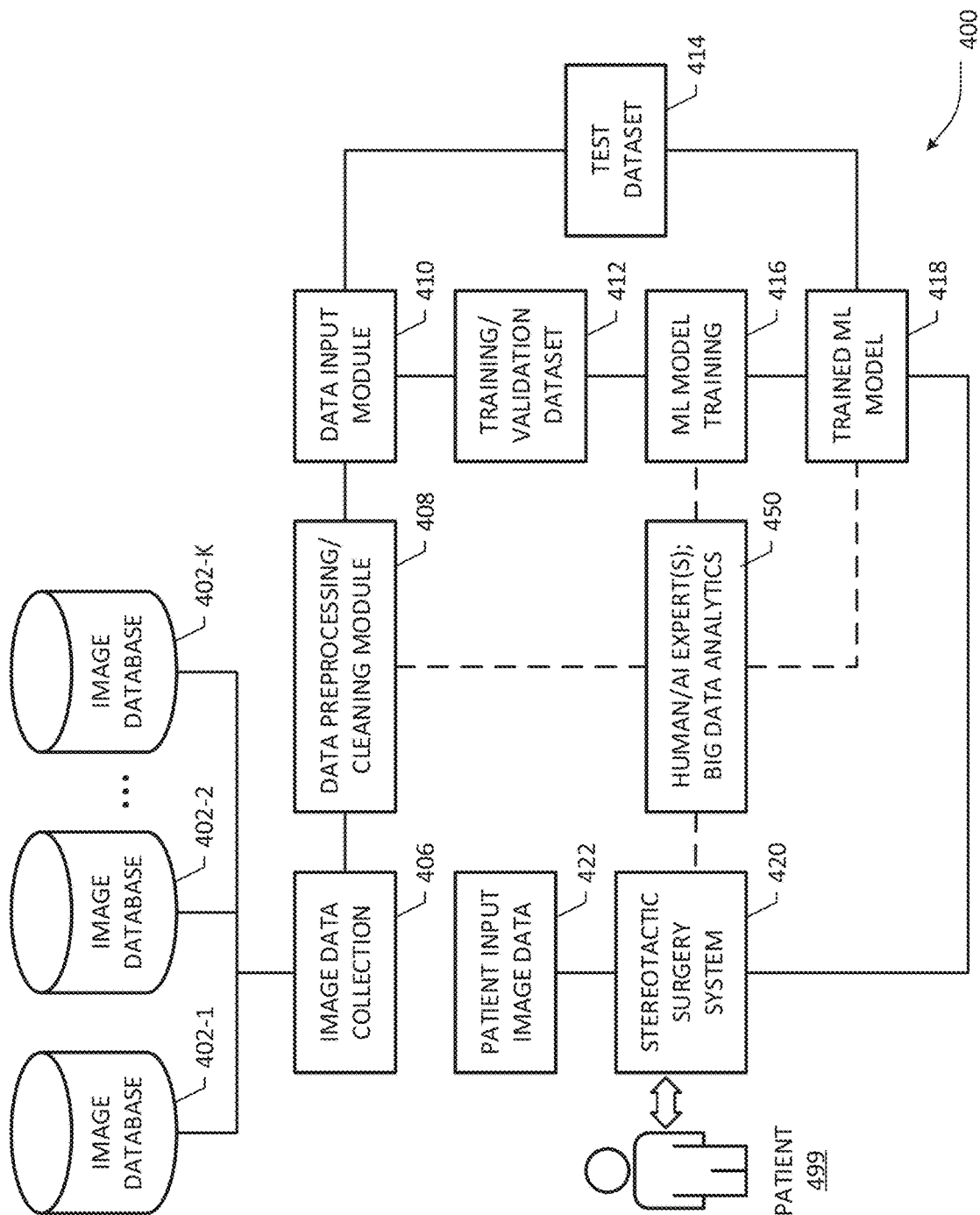
FIG. 4 depicts a block diagram of an apparatus, node, or a computing platform for training, testing and generating a validated/tested CNN/ANN process or engine operative in conjunction with a stereotactic surgery system for purposes of an example embodiment of the present patent disclosure.

Turning attention to FIG. 4, depicted therein is a block diagram of an apparatus, node, or computing platform 400 for training, testing and generating a validated/tested CNN/ANN process or engine operative in conjunction with a stereotactic surgery system for purposes of an example embodiment of the present patent disclosure. As illustrated, a data collection module 406 is operative to obtain medical imaging data relating to human cranial anatomy from a number of public and/or private repositories 402-1 to 402-K containing image slices in various imaging modalities. A data preprocessing or cleaning module 408 is operative to perform data cleaning operations as well as data augmentation processes, which may be guided/unguided or supervised/unsupervised by human or AI-based experts 450 having knowledge and domain expertise relative to the human anatomy and neuroradiology, with respect to the input data obtained by the data collection module 406. Accordingly, a modified image dataset may be generated by the data preprocessing/cleaning module 408, which may be partitioned by an input module 410 as one or more training datasets, validation datasets and test datasets. As set forth elsewhere in the present patent disclosure, for purposes of some embodiments herein a training dataset may be a dataset of input images or slices (processed, preprocessed or unprocessed) used during the learning process of a CNN/ANN and is used to fit the parameters of the CNN/ANN. A validation dataset is a dataset of images/slices used to tune the hyperparameters (i.e., the architecture) of a classifier. A test dataset is a dataset that may be independent of the training dataset but follows the same probability distribution as the training dataset in some implementations. By way of illustration, a training/validation dataset 412 is exemplified as a labeled dataset that may be provided to a training process 416 with respect to training and validating an ML image classifier for predicting the ROI/ROA features in human brain scan images. Depending on the particular ML implementation architecture, ML model training 416 may involve one or more iterations, which in some instances may include (semi)supervised learning based on input from human/AI experts, such that a trained ML model 418 that is appropriately fitted is obtained i.e., resulting in a model without underfitting or overfitting. In one embodiment, the foregoing operations may be provided as part of the ML training stage or aspect of an example implementation. In a subsequent or separate phase, the fitted/trained ML model 418 may be used in conjunction with additional or partitioned input datasets 414 as test data for generating predictive output. As one skilled in the art will recognize, at least a portion of the foregoing operations may be performed offline and/or by different computing modules of a distributed computing platform depending on implementation. After training, testing and validating the ML model 418, it may be executed in conjunction with a suitable stereotactic surgery system 420 operative for determining an image-guided trajectory based on one or more co-registered pre-operative brain images 422 of a patient 499.

Figure 5:
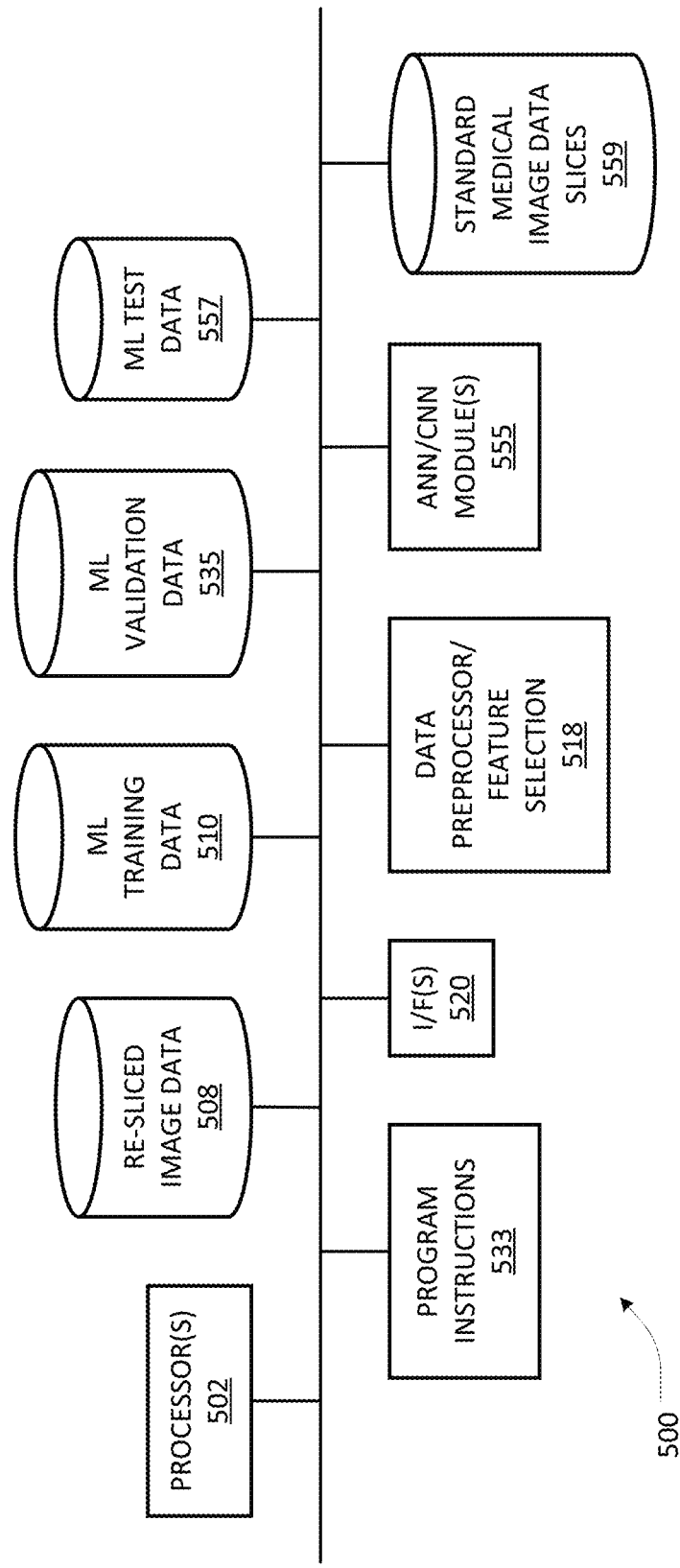
FIG. 5 depicts a block diagram of a system involving a plurality of modules that may be configured as an integrated or distributed platform for effectuating ML-based electrode trajectory planning according to an example embodiment of the present patent disclosure.

FIG. 5 depicts a block diagram involving a plurality of modules that may be configured as a system or apparatus 500 for effectuating ML-based electrode trajectory planning according to another view of an example embodiment of the present patent disclosure. One or more processors 502 may be operatively coupled to various modules that may be implemented in persistent memory for executing suitable program instructions or code portions (e.g., code portion 533) with respect to effectuating any of the processes, methods and/or flowcharts set forth hereinabove in association with one or more modules, e.g., data preprocessing and/or augmentation module 518, ANN/CNN module(s) 555 (where ML-based image classification and feature prediction is implemented), etc. One or more databases may be provided as part of or in association with apparatus 500 for storing various data, e.g., ML training data 510, ML validation data 535, ML test data 557, which may be derived from re-sliced/augmented image data 508 and standard orientation image data 559, wherein at least some of the data may be obtained from different sources and imaging modalities pursuant to federated learning. Although not specifically shown herein, one or more Big Data analytics modules may also be interfaced with apparatus 500 for providing additional predictive analytics with respect to image classification. Depending on the implementation and system integration, various network interfaces (I/Fs) 520 may be provided for interfacing with components such as integrated surgical stations including stereotactic navigation systems, medical imaging systems, external databases, etc.

At least a portion of an ML-based electrode trajectory planning system disclosed herein may also be virtualized and/or architected in a cloud-computing environment comprising a shared pool of configurable resources deployed as a medical image processing datacenter according to some embodiments.

Figure 6:
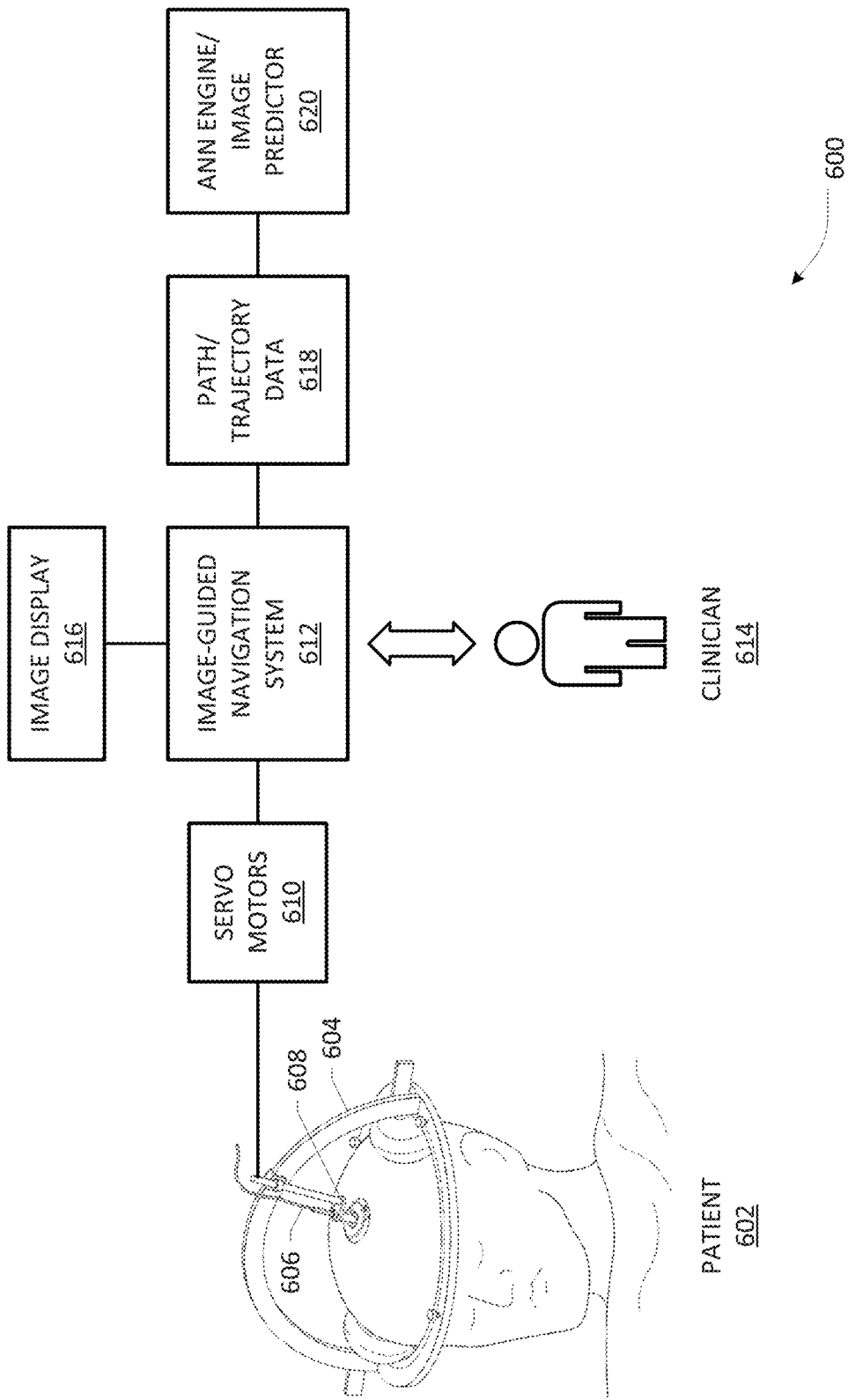
FIG. 6 depicts an automated stereotactic surgery system for facilitating a DBS electrode implant procedure according to an example embodiment of the present patent disclosure.

FIG. 6 depicts an automated stereotactic surgery system 600 for facilitating a DBS electrode implant procedure according to an example embodiment of the present patent disclosure. An ML-based image predictor 620 may be configured to generate an optimal trajectory based on building a virtual electrode scene responsive to analyzing an input MRI brain image of a patient 602 as described hereinabove. Path/trajectory data 618 generated by the image predictor 620 may be provided to an image-guided navigation system 612 operated by a clinician or surgeon 614, wherein a co-registered CT scan may be used in association with the patient's MRI image to obtain appropriate coordinates for stereotactic surgery. Suitable control output may be provided by the image-guided navigation system 612, automatically or under surgical supervision, to one or more servo motors 610 operative to control a stereotactic frame 604 having an implantable instrumentation column 608 containing a DBS lead 606. Although a center-of-arc stereotactic frame 604 is exemplified in FIG. 6, which may encompass the entire head of patient 602, a frameless or microframe arrangement that attaches to only a small portion of the patient's skull surrounding a burr hole may be provided as a trajectory guiding apparatus in additional or alternative implementations for advancing the instrumentation column under navigational control. As the instrumentation is advanced, its trajectory may be monitored, e.g., based on tracking on prerecorded imaging or live imaging, via a display monitor 616. If lateral/axial adjustment with respect to the trajectory path is needed as the instrumentation is advanced towards a predetermined target area in the patient's brain, appropriate translational/rotational movement controls of the servo motors 610 may be effectuated accordingly to reorient the stereotactic frame apparatus 604.

FIGS. 7A and 7B depict a DBS therapy system and associated lead arrangement having a plurality of electrodes that may be implanted using an image identification and trajectory planning system according to an example embodiment of the present patent disclosure. Example DBS therapy system 700A includes a pulse generator 702, which may be typically implemented using a metallic housing that encloses circuitry for generating one or more electrical pulse sequences for application to the brain tissue of a patient. Control circuitry, communication circuitry, and a rechargeable battery (not shown) are also typically included within pulse generator 702.

In one arrangement, pulse generator 702 may be configured to wirelessly communicate with a programmer device 703. In general operation, programmer device 703 enables a clinician to control the pulse generating operations of pulse generator 702. The clinician can select electrode combinations, pulse amplitude, pulse width, frequency parameters, and/or the like using the user interface of programmer device 703. As is known in the art, the parameters can be defined in terms of "stim sets," "stimulation programs," or any other suitable format. Programmer device 703 responds by communicating the parameters to pulse generator 702 and pulse generator 702 modifies its operations to generate stimulation pulses according to the communicated parameters.

One or more leads 706 are electrically coupled to the circuitry within pulse generator 702 using a hermetically sealed header 704. Example lead 706 may include terminals (not shown) that are adapted to electrically connect with electrical connectors disposed within header 704. The terminals are electrically coupled to conductors (not shown) within the lead body of lead 706, which conduct pulses from the proximal end to the distal end of lead 706. The conductors are also electrically coupled to one or more electrodes 708 to apply the pulses to tissue of the patient. Lead 701 can be utilized for any suitable DBS therapy using precise targeting of tissue for stimulation identified by the electrode trajectory planning system of the present patent disclosure. For example, the distal end of lead 701 may be implanted within a target location for treating a variety of disabling neurological symptoms, most commonly the debilitating motor symptoms of Parkinson's disease (PD), such as tremor, rigidity, stiffness, slowed movement, and walking problems, as well as conditions such as essential tremor, dystonia, focal epilepsy (epilepsy that originates in just one part of the brain), etc., in addition to mood and anxiety disorders that may be treated by targeting areas such as nucleus accumbens, subgenual cingulate cortex and ventral capsule/ventral striatum in a patient's brain.

A particularized view 700B of the distal end of lead 706 is illustrated in FIG. 7B, wherein a plurality of electrodes 710-1 to 710-N may comprise multiple segmented electrodes. It will be appreciated that the use of segmented electrodes permits the clinician to more precisely control the electrical field generated by the stimulation pulses and, hence, to more precisely control the stimulation effect in surrounding tissue. In some arrangements, electrodes 710-1 to 710-N may alternatively or additionally include one or more ring electrodes or a tip electrode. Any of the electrode assemblies including segmented and/or unsegmented electrodes discussed herein can be used in a DBS implant procedure aided by way of an image-guided navigation apparatus operating in conjunction with the ML-based trajectory planning system of present patent disclosure. The term "segmented electrode" is distinguishable from the term "ring electrode." As used herein, the term "segmented electrode" refers to an electrode of a group of electrodes that are positioned at approximately the same longitudinal location along the longitudinal axis of a lead and that are angularly positioned about the longitudinal axis so they do not overlap and are electrically isolated from one another. For example, at a given position longitudinally along the lead body, three electrodes can be provided with each electrode covering respective segments of less than 120° about the outer diameter of the lead body. By selecting between such electrodes, the electrical field generated by stimulation pulses can be more precisely controlled and, hence, stimulation of undesired tissue can be more easily avoided. It should be appreciated, however, that regardless of the type of electrodes used, the placement and orientation of a select electrode may be better facilitated by obtaining more accurate ROI/ROA identification using the ML-based feature identification and trajectory planning system of the present patent disclosure. Additional details regarding DBS leads and electrodes, which may be used in conjunction with some embodiments herein may be found in, e.g., (i) U.S. Pat. No. 9,238,134, entitled "ELECTRICAL STIMULATION SYSTEM AND ASSOCIATED APPARATUS FOR SECURING AN ELECTRICAL STIMULATION LEAD IN POSITION IN A PERSON'S BRAIN"; (ii) U.S. Pat. No. 8,225,504, entitled "MEDICAL LEADS WITH SEGMENTED ELECTRODES AND METHODS OF FABRICATION THEREOF"; and (iii) U.S. Pat. No. 8,463,387, entitled "STIMULATION OF THE AMYGDALOHIPPOCAMPAL COMPLEX TO TREAT NEUROLOGICAL CONDITIONS", each of which is incorporated herein by reference.

Figure 8:
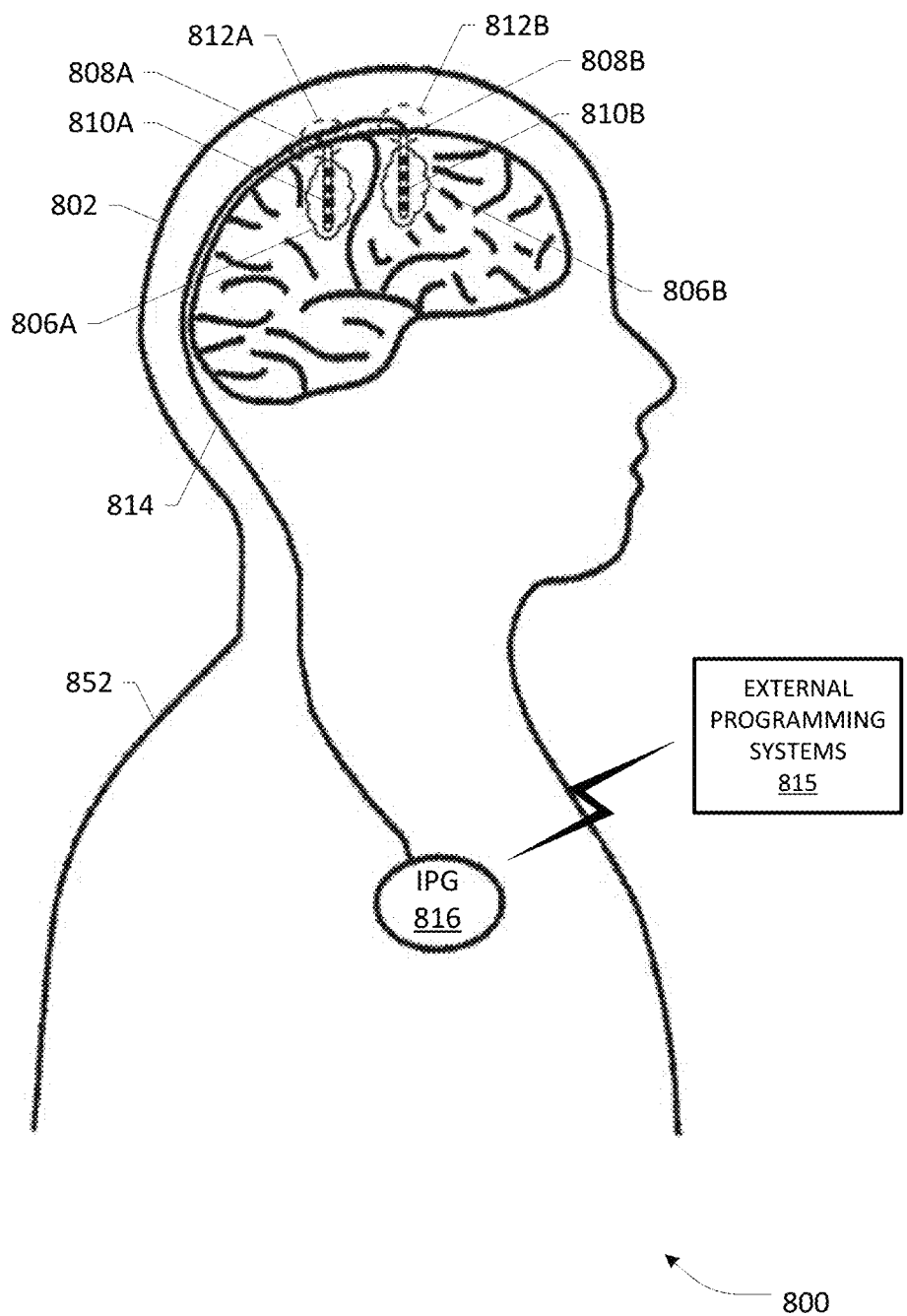
FIG. 8 is an illustrative diagram of a patient having one or more therapy leads implanted in different brain regions using a trajectory guide apparatus aided by an embodiment of the present disclosure according to the teachings herein.

FIG. 8 is an illustrative diagram of a patient having one or more therapy leads implanted in different brain regions using a trajectory guide apparatus aided by an embodiment of the of the present disclosure according to the teachings herein. As illustrated, a patient 852 is shown with two regions or targets of interest 806A and 800B of the patient's brain 804 that are implanted with respective DBS leads 808A and 808B, each guided and advanced by a trajectory guide apparatus controlled by the ML-based electrode trajectory planning system of the present patent disclosure. Prior to the implant procedure, respective burr holes 812A and 812B may be drilled in the patient's cranium 802 based on the respective entry point coordinate sets obtained as described previously with respect to a desired therapy application, which may be spaced proximate to each other given that an example trajectory guide apparatus may be optimized to have a small form factor while providing sufficient structural strength to be firmly attached to the cranium 802. After completion of a suitable burr hole creation procedure, fiducial markers or reference points may be affixed to the patient's skull. As noted previously, any suitable imaging technology can be utilized such as MRI systems, CT systems, etc., for obtaining pre-operative and/or intra-operative imaging data of the patient's brain. The imaging may also involve functional analysis of the brain in response to specific stimuli. For example, a functional MRI process may be performed in which stimuli is provided to the patient and the MRI imaging is utilized to identify the specific structures in the brain that respond to the stimuli. Based upon the imaging information, the trained ML-based trajectory planning scheme may be executed to provide real time target location information and optimal path data to a stereotactic surgery system including the guiding apparatus as described. After completing the guided implantation of leads 808A/808B, the burr holes 812A and 812B may be capped and secured for routing the leads 808A/808B under the scalp of the patient 852. In one arrangement, electrical traces for the leads 808A/808B may be combined into a single lead body 814 that is routed subcutaneously to be coupled to an implanted pulse generator (IPG) 816, which may be electrically and/or telemetrically coupled to an external programming system 815 to provide appropriate therapy.

In the above-description of various embodiments of the present disclosure, it is to be understood that the terminology used herein is for the purpose of describing particular embodiments only and is not intended to be limiting of the invention. Unless otherwise defined, all terms (including technical and scientific terms) used herein have the same meaning as commonly understood by one of ordinary skill in the art to which this invention belongs. It will be further understood that terms, such as those defined in commonly used dictionaries, should be interpreted as having a meaning that is consistent with their meaning in the context of this specification and the relevant art and may not be interpreted in an idealized or overly formal sense expressly so defined herein.

At least some example embodiments are described herein with reference to one or more circuit diagrams/schematics, block diagrams and/or flowchart illustrations. It is understood that such diagrams and/or flowchart illustrations, and combinations of blocks in the block diagrams and/or flowchart illustrations, can be implemented by any appropriate circuitry configured to achieve the desired functionalities. Accordingly, example embodiments of the present disclosure may be embodied in hardware and/or in software (including firmware, resident software, micro-code, etc.) operating in conjunction with suitable processing units or microcontrollers, which may collectively be referred to as "circuitry," "a module" or variants thereof. An example processing unit or a module may include, by way of illustration, a general purpose processor, a special purpose processor, a conventional processor, a digital signal processor (DSP), a plurality of microprocessors, one or more microprocessors in association with a DSP core, a controller, a microcontroller, Application Specific Integrated Circuits (ASICs), Field Programmable Gate Array (FPGA) circuits, any other type of integrated circuit (IC), and/or a state machine, as well as programmable system devices (PSDs) employing system-on-chip (SoC) architectures that combine memory functions with programmable logic on a chip that is designed to work with a standard microcontroller. Example memory modules or storage circuitry may include volatile and/or non-volatile memories such as, e.g., random access memory (RAM), electrically erasable/programmable read-only memories (EEPROMs) or UV-EPROMS, one-time programmable (OTP) memories, Flash memories, static RAM (SRAM), etc.

Further, in at least some additional or alternative implementations, the functions/acts described in the blocks may occur out of the order shown in the flowcharts. For example, two blocks shown in succession may in fact be executed substantially concurrently or the blocks may sometimes be executed in the reverse order, depending upon the functionality/acts involved. Moreover, the functionality of a given block of the flowcharts and/or block diagrams may be separated into multiple blocks and/or the functionality of two or more blocks of the flowcharts and/or block diagrams may be at least partially integrated. Also, some blocks in the flowcharts may be optionally omitted. Furthermore, although some of the diagrams include arrows on communication paths to show a primary direction of communication, it is to be understood that communication may occur in the opposite direction relative to the depicted arrows. Finally, other blocks may be added/inserted between the blocks that are illustrated.

It should therefore be clearly understood that the order or sequence of the acts, steps, functions, components or blocks illustrated in any of the flowcharts depicted in the drawing Figures of the present disclosure may be modified, altered, replaced, customized or otherwise rearranged within a particular flowchart, including deletion or omission of a particular act, step, function, component or block. Moreover, the acts, steps, functions, components or blocks illustrated in a particular flowchart may be inter-mixed or otherwise inter-arranged or rearranged with the acts, steps, functions, components or blocks illustrated in another flowchart in order to effectuate additional variations, modifications and configurations with respect to one or more processes for purposes of practicing the teachings of the present patent disclosure.

Although various embodiments have been shown and described in detail, the claims are not limited to any particular embodiment or example. None of the above Detailed Description should be read as implying that any particular component, element, step, act, or function is essential such that it must be included in the scope of the claims. Where the phrases such as "at least one of A and B" or phrases of similar import are recited, such a phrase should be understood to mean "only A, only B, or both A and B." Reference to an element in the singular is not intended to mean "one and only one" unless explicitly so stated, but rather "one or more." Moreover, the terms "first," "second," and "third," etc. employed in reference to elements or features are used merely as labels, and are not intended to impose numerical requirements, sequential ordering or relative degree of significance or importance on their objects. All structural and functional equivalents to the elements of the above-described embodiments that are known to those of ordinary skill in the art are expressly incorporated herein by reference and are intended to be encompassed by the present claims. Accordingly, those skilled in the art will recognize that the exemplary embodiments described herein can be practiced with various modifications and alterations within the spirit and scope of the claims appended below.

The invention claimed is:

1. A computer-implemented method of electrode trajectory planning for deep brain stimulation (DBS), the method comprising:
   obtaining a set of medical imaging data pertaining to human cranial anatomy, the set of medical imaging data sampled from a plurality of humans in one or more imaging modalities, wherein the medical imaging data comprises image slices taken along at least one of coronal, sagittal and axial planes relative to the human cranial anatomy;
   re-slicing at least a portion of the medical imaging data through one or more planes that are at an angular orientation with respect to at least one of the coronal, sagittal and axial planes, thereby obtaining re-sliced medical imaging data;
   training a first artificial neural network (ANN) engine using a portion of the medical imaging data that has not been re-sliced and a portion of the re-sliced medical imaging data, wherein the medical imaging data is appropriately labeled, to obtain a first validated and tested ANN engine configured to distinguish one or more regions of interest (ROIs) from one or more regions of avoidance (ROAs) in a human brain image;
   executing the first ANN engine, in response to an input image of a patient's brain obtained using a particular imaging modality, to identify at least one particular ROI in the patient's brain to facilitate planning of an optimal trajectory for implanting a DBS lead having one or more electrodes in the at least one particular ROI while avoiding any ROAs identified in the patient's brain;
   blending two or more co-registered image slices selected from at least one of the medical imaging data that has not been re-sliced or the portion of the re-sliced medical imaging data to obtain hybrid image slices;
   training a second ANN engine using a portion of the hybrid image slices to obtain a second validated and tested ANN engine configured to distinguish one or more ROIs from one or more ROAs in the human brain image; and
   executing the first and second ANN engines separately with respect to the input image of the patient's brain and combining the ROI and ROA identifications obtained respectively therefrom for improving quality of identification of the at least one particular ROI.

2. The method as recited in claim 1, wherein training the first ANN comprises
   training the first ANN engine using a portion of the hybrid image slices in addition to the medical imaging data that has not been re-sliced and the portion of the re-sliced medical imaging data.

3. The method as recited in claim 1, further comprising performing, prior to the training, morphological image processing of image slices of the medical imaging data that has not been re-sliced or the portion of the re-sliced medical imaging data, wherein the morphological image processing includes at least one of edge detection, contrast boosting and shape detection.

4. The method as recited in claim 1, further comprising performing a dropout technique with respect to the first ANN engine wherein a select number of computational nodes are dropped from a particular neural network layer in each training epoch.

5. The method as recited in claim 1, further comprising:
   building an electrode scene with respect to the at least one particular ROI of the patient's brain image for placing the DBS lead thereat; and
   determining the optimal trajectory for implanting the DBS lead in the patient's brain relative to a particular electrode of the DBS lead.

6. The method as recited in claim 5, further comprising:
   co-registering a computed tomography (CT) image of the patient's brain with the input image of the patient having the at least one particular ROI identified for stimulation, wherein the input image of the patient's brain comprises one of a pre-operative or intra-operative magnetic resonance imaging (MRI) scan; and obtaining an entry point coordinate set and a target point coordinate set with respect to the patient's brain for performing an implant procedure to implant the DBS lead using the optimal trajectory, wherein the entry point coordinate set is operative to identify a burr hole location on the patient's cranium and the target point coordinate set is operative to identify a location relative to the at least one particular ROI in the patient's brain.

7. The method as recited in claim 6, further comprising:
providing the entry point coordinate set, the target point coordinate set and data relating to the optimal trajectory to a stereotactic surgery system including a guiding apparatus containing the DBS lead; and
automatically guiding the DBS lead to the at least one particular ROI based on the entry point coordinate set, the target point coordinate set and the data relating to the optimal trajectory data to place the particular electrode proximate to the at least one particular ROI.

8. A computer-implemented system configured to facilitate electrode trajectory planning for deep brain stimulation (DBS), the system comprising:
one or more processors; and
a persistent memory having program instructions stored thereon, the program instructions, when executed by the one or more processors, configured to perform:
obtaining a set of medical imaging data pertaining to human cranial anatomy, the set of medical imaging data sampled from a plurality of humans in one or more imaging modalities, wherein the medical imaging data comprises image slices taken along at least one of coronal, sagittal and axial planes relative to the human cranial anatomy;
re-slicing at least a portion of the medical imaging data through one or more planes that are at an angular orientation with respect to at least one of the coronal, sagittal and axial planes, thereby obtaining re-sliced medical imaging data;
training a first artificial neural network (ANN) engine using a portion of the medical imaging data that has not been re-sliced and a portion of the re-sliced medical imaging data, wherein the medical imaging data is appropriately labeled, to generate a first validated and tested ANN engine configured to distinguish one or more regions of interest (ROIs) from one or more regions of avoidance (ROAs) in a human brain image;
in response to an input image of a patient's brain obtained using a particular imaging modality, executing the first ANN engine to identify at least one particular ROI in the patient's brain to facilitate planning of an optimal trajectory for implanting a DBS lead having one or more electrodes in the at least one particular ROI while avoiding any ROAs identified in the patient's brain;
blending two or more co-registered image slices selected from at least one of the medical imaging data that has not been re-sliced or the portion of the re-sliced medical imaging data to obtain hybrid image slices;
training a second ANN engine using a portion of the hybrid image slices to generate a second validated and tested ANN engine configured to distinguish between one or more ROIs from one or more ROAs in the human brain image; and
executing the first and second ANN engines separately with respect to the input image of the patient's brain and combining the ROI and ROA identifications obtained respectively therefrom for improving quality of identification of the at least one particular ROI.

9. The system as recited in claim 8, wherein, to the train the first ANN engine, the program instructions further comprise instructions configured to perform:
training the first ANN engine using a portion of the hybrid image slices in addition to the medical imaging data that has not been re-sliced and the portion of the re-sliced medical imaging data.

10. The system as recited in claim 8, wherein the program instructions further comprise instructions configured to perform, prior to the training, morphological image processing of image slices of the medical imaging data that has not been re-sliced or the portion of the re-sliced medical imaging data, wherein the morphological image processing includes at least one of edge detection, contrast boosting and shape detection.

11. The system as recited in claim 8, wherein the program instructions further comprise instructions configured to perform a dropout technique with respect to the first ANN engine wherein a select number of computational nodes are dropped from a particular neural network layer in each training epoch.

12. The system as recited in claim 8, wherein the program instructions further comprise instructions configured to perform:
building an electrode scene with respect to the at least one particular ROI of the patient's brain image for placing the DBS lead thereat; and
determining the optimal trajectory for implanting the DBS lead in the patient's brain relative to a particular electrode of the DBS lead.

13. The system as recited in claim 12, wherein the program instructions further comprise instructions configured to perform:
co-registering a computed tomography (CT) image of the patient's brain with the input image of the patient having the at least one particular ROI identified for stimulation, wherein the input image of the patient's brain comprises one of a pre-operative or intra-operative magnetic resonance imaging (MRI) scan; and
determining an entry point coordinate set and a target point coordinate set with respect to the patient's brain for performing an implant procedure to implant the DBS lead using the optimal trajectory, wherein the entry point coordinate set is operative to identify a burr hole location on the patient's cranium and the target point coordinate set is operative to identify a location relative to the at least one particular ROI in the patient's brain.

14. The system as recited in claim 13, further comprising a stereotactic surgery system including a guiding apparatus containing the DBS lead, and wherein the program instructions further comprise instructions configured to perform:
providing the entry point coordinate set, the target point coordinate set and data relating to the optimal trajectory to the stereotactic surgery system; and
automatically guiding the DBS lead to the at least one particular ROI based on the entry point coordinate set, the target point coordinate set and the data relating to the optimal trajectory data to place the particular electrode proximate to the at least one particular ROI.

* * * * *